US012788626B2

(12) United States Patent
Yeh

(10) Patent No.: US 12,788,626 B2
(45) Date of Patent: Nov. 10, 2026

(54) COOLING PAD AND METHODS OF MAKING AND USING THE SAME

(71) Applicant: EZTIA CORP., Diamond Bar, CA (US)

(72) Inventor: Tiffany Yeh, Diamond Bar, CA (US)

(73) Assignee: EZTIA CORP., Diamond Bar, CA (US)

( * ) Notice: Subject to any disclaimer, the term of this patent is extended or adjusted under 35 U.S.C. 154(b) by 103 days.

(21) Appl. No.: 18/913,091

(22) Filed: Oct. 11, 2024

(65) Prior Publication Data

US 2026/0115038 A1 Apr. 30, 2026

Related U.S. Application Data

(63) Continuation of application No. PCT/US2023/036005, filed on Oct. 27, 2023.
(Continued)

(51) Int. Cl.
*A61F 7/02* (2006.01)
*A61F 7/00* (2006.01)

(52) U.S. Cl.
CPC ........ *A61F 7/02* (2013.01); *A61F 2007/0098* (2013.01); *A61F 2007/0219* (2013.01);
(Continued)

(58) Field of Classification Search
CPC ................ A61F 7/02; A61F 2007/0219; A61F 2007/0226
See application file for complete search history.

(56) References Cited

U.S. PATENT DOCUMENTS 5,204,110 A 4/1993 Cartmell et al.
2003/0167556 A1* 9/2003 Kelley ................ A45D 44/002 2/206
(Continued)

FOREIGN PATENT DOCUMENTS

CN 109504310 A 3/2019
CN 210472144 U 5/2020
(Continued)

OTHER PUBLICATIONS

Cui, S., et al. (2016). "Bio-inspired effective and regenerable building cooling using tough hydrogels." Applied Energy, 168: 332-339.
(Continued)

*Primary Examiner* — Sean W Collins
(74) *Attorney, Agent, or Firm* — Duane Morris LLP

(57) ABSTRACT

A cooling pad, a method of making the cooling pad, and a method of using the cooling pad are provided. Such a cooling pad includes a hydrogel layer, a protective backing layer coated with a first adhesive layer, and a second adhesive layer. The backing layer coated with the first adhesive layer, and the second adhesive layer are disposed on two different sides of the hydrogel layer. The hydrogel layer comprises a base polymer as a first base ingredient for the hydrogel layer, a second base ingredient for the hydrogel layer, and an additive or filler, which may include a moisture absorbing agent, a stabilizing agent, an antimicrobial agent, a photothermal agent, or any other additive or filler, or any combination thereof.

20 Claims, 8 Drawing Sheets

Related U.S. Application Data

(60) Provisional application No. 63/381,776, filed on Nov. 1, 2022, provisional application No. 63/482,604, filed on Feb. 1, 2023.

(52) U.S. Cl.
CPC . *A61F 2007/022* (2013.01); *A61F 2007/0226* (2013.01); *A61F 2007/0258* (2013.01); *A61F 2007/0263* (2013.01); *A61F 2007/0282* (2013.01)

(56) References Cited

U.S. PATENT DOCUMENTS

| | | | |
|---|---|---|---|
| 2004/0153040 | A1 | 8/2004 | Martineau et al. |
| 2004/0241241 | A1 | 12/2004 | Lopatin |
| 2008/0208347 | A1 | 8/2008 | Muratoglu et al. |
| 2009/0110732 | A1 | 4/2009 | Jabbari |
| 2016/0185712 | A1 | 6/2016 | Casasanta, III et al. |
| 2017/0128271 | A1* | 5/2017 | Freer ................. A61F 13/00059 |
| 2018/0244858 | A1 | 8/2018 | Illeperuma et al. |
| 2021/0170068 | A1* | 6/2021 | Sthengel ............. A61F 13/0253 |
| 2021/0353830 | A1* | 11/2021 | Sun .......................... C08J 3/246 |
| 2022/0134608 | A1 | 5/2022 | Staebler et al. |
| 2022/0280336 | A1* | 9/2022 | Smith ................... A61F 7/0085 |

FOREIGN PATENT DOCUMENTS

| | | | |
|---|---|---|---|
| CN | 112957456 A | 6/2021 | |
| WO | WO-2015145117 A1 * | 10/2015 | ......... A61F 13/0206 |

OTHER PUBLICATIONS

Feng, C., et al. (2021). "Bilayer porous polymer for efficient passive building cooling." Nano Energy, 85: 105971.

Ferber, S., et al. (2018). "Evaporative Cooling Hydrogel Packaging for Storing Biologics Outside of the Cold Chain." Adv Healthc Mater, 7(14): e1800220.

Gogoi, P., et al. (2020). "Ductile cooling phase change material." Nanoscale Advances 2(9): 3900-3905.

Ji, Y., et al. (2022). "Skin inspired thermoresponsive polymer for constructing self-cooling system." Energy Conversion and Management 254: 115251.

Li, J., et al. (2017). "Tough adhesives for diverse wet surfaces." Science 357(6349): 378-381.

Li, R., et al. (2020). "Photovoltaic panel cooling by atmospheric water sorption-evaporation cycle." Nature Sustainability 3(8): 636-643.

Lu, Z., et al. (2020). "Passive Sub-Ambient Cooling from a Transparent Evaporation-Insulation Bilayer." Joule 4(12): 2693-2701.

Rotzetter, A. C. C., et al. (2012). "Thermoresponsive Polymer Induced Sweating Surfaces as an Efficient Way to Passively Cool Buildings." Advanced Materials 24(39): 5352-5356.

Shi, W., et al. (2022). "Improved Cooling Performance of Hydrogel Wound Dressings via Integrating Thermal Conductivity and Heat Storage Capacity for Burn Therapy." Biomacromolecules 23(3): 889-902.

Takegami, Y., et al. (2011). "Synthesis and characterization of high-quality skin-cooling sheets containing thermosensitive poly(N-isopropylacrylamid)." J Biomed Mater Res B Appl Biomater 98(1): 110-113.

Xu, Z., et al. (2018). "Sunlight-Induced Photo-Thermochromic Supramolecular Nanocomposite Hydrogel Film for Energy-Saving Smart Window." Solar RRL 2(11): 1800204.

Yu, Z., et al. (2021). "Flame-retardant PNIPAAm/sodium alginate/polyvinyl alcohol hydrogels used for fire-fighting application: Preparation and characteristic evaluations." Carbohydrate Polymers 255: 117485.

Zhao, B., et al. (2022). "Bio-inspired BC aerogel/PVA hydrogel bilayer gel for enhanced daytime sub-ambient building cooling." Cellulose 29(14): 7775-7787.

Zhou, G., et al. (2022). "Synthesis and performance of a new temperature-sensitive and super-absorbent fire prevention hydrogel based on ultrasonic method." Colloids and Surfaces A: Physicochemical and Engineering Aspects 640: 128399.

International Search Report and Written Opinion, mailed Mar. 26, 2024, in related International PCT Application No. PCT/US2023/036005.

* cited by examiner

COOLING PAD AND METHODS OF MAKING AND USING THE SAME

PRIORITY CLAIM AND CROSS-REFERENCE

This application is a continuation of International Application No. PCT/US2023/036005, filed Oct. 26, 2023, which claims the priority benefit of U.S. Provisional Application No. 63/381,776, filed Nov. 1, 2022, and U.S. Provisional Application No. 63/482,604, filed Feb. 1, 2023, which applications are expressly incorporated by reference herein in their entirety.

FIELD OF THE INVENTION

The disclosure relates to a cooling pad or patch generally. More particularly, the disclosed subject matter relates to a cooling pad or patch configured to contact skin of a subject in need such as a human and prevent heat related illness and/or relieve pain or discomfort, a pack comprising the cooling pad or patch, and method of making the same.

BACKGROUND

Building cooling takes up a large proportion of residential and commercial energy consumption. Buildings need to adapt to heat stress caused by climate change-exacerbated extreme temperatures. Cooling films may be used as new-generation building energy saving materials.

Cooling target locations of superficial blood circulation on a human subject, such as the inner wrist, nape of neck or torso, can decrease the core body temperature of the subject and prevent the subject from overheating and developing heat-related illnesses in the setting of high environmental temperatures and/or physical activity.

Cooling of an injury site of a subject in need, for example, using ice, after injury is important in reducing the swelling and inflammation around the site of injury and speeding recovery. After the acute phase has passed, recovery is often aided by episodes of heating. Athletes have also learned about the importance of using cooling to assist in recovery after training. Cooling reduces pain, reduces tissue damage and has also been shown to have a positive effect on performance.

A cooling pad is also used to decrease temperature of a body part having infection in a patient. In addition, a cooling pad is used to reduce organ metabolism, for example, during cardiac surgery to reduce heart metabolism.

Active cooling uses electricity to power a coolant, whether it's water or air, to dissipate heat from a surface.

Alginate-acrylamide hydrogel has a double network structure, which may have covalent crosslinks and ionic crosslinks. See e.g., A. Pragya, et al., "Dynamic cross-linking of an alginate-acrylamide tough hydrogel system: time-resolved in situ mapping of gel self-assembly," *RSC Adv.* 2021, 11, 10710. Composite materials including alginate-acrylamide based dual network hydrogel have also been explored for cooling uses. See P. Gogoi, et al., "Ductile cooling phase change material," *Nanoscale Adv.,* 2020, 2, 3900; International Application WO 2021/178601.

SUMMARY

The present disclosure provides a cooling pad (or patch), a pack comprising the cooling pad enclosed therein, a method of making the cooling pad, and a method of using the cooling pad.

In one aspect, the present disclosure provides a cooling pad (or patch). Such a cooling pad comprises a hydrogel layer configured to provide cooling, a protective backing layer that interfaces with the ambient environment and/or clothing, a first adhesive layer between the hydrogel layer and the protective backing layer, and a second adhesive layer. The backing layer coated with the first adhesive layer (i.e., a glue) and the second adhesive layer are disposed on two different sides of the hydrogel layer. The protective backing layer and the first adhesive layer are disposed on a first side of the hydrogel layer. The second adhesive layer is disposed on a second side of the hydrogel layer. The second side is opposite to the first surface.

The hydrogel layer comprises a solid gel portion and a liquid portion. The liquid portion comprises water. The liquid portion is embedded and distributed within the solid gel portion. The solid gel portion comprises a base polymer as a first base ingredient for the hydrogel layer, moieties of a second base ingredient for the hydrogel layer, and an additive or filler. The second base ingredient is crosslinked or copolymerized with the first base polymer for the hydrogel layer.

Examples of the base polymer in the hydrogel layer include, but are not limited to, polyacrylamide (PAM), poly(N-isopropylacrylamide) (PNIPAM), polyvinyl alcohol (PVA), oligo(ethylene glycol) methacrylate (OEGMA), 2-(2-methoxyethoxy) ethyl methacrylate (MEO2MA), Xylan, carboxymethylcellulose sodium, and any combination thereof.

Examples of the second base ingredient for the hydrogel layer include, but are not limited to, a bisacrylamide, calcium alginate, hyaluronic acid, 2-acrylamido-2-methylpropane sulfonic acid (AMPS), ethylene glycol-modified pillar [5]arene, and any combination thereof. The second base ingredient may include a crosslinker and/or a curatives for forming crosslinking structure or structures. One example is a bisacrylamide. In some embodiments, the second base ingredient may be used to form a hydrogel having two types of network structure, for example, covalent and ionic crosslinking structures. In some embodiments, the base polymer and related crosslinking agent are used to provide a hydrogel having only one type of crosslinking network structure such as a covalent crosslinking network structure.

The additive or filler may include a moisture absorbing agent, a stabilizing agent, an antimicrobial agent, a photothermal agent, and any combination thereof. Examples of the additive or filler include, but are not limited to, $CaSO_4$, calcium chloride hexahydrate, LiCl, KCl, zinc oxide, $TiO_2$, carbon nanotube, $CaCl_2$, LiBr, $MgCl_2$, silica microsphere, antimony-tin oxide nanoparticle, graphene oxide, tungsten bronze nanorods, and any combination thereof. The fillers can be nanoparticle or microparticles.

In some embodiments, the additive or filler comprises a moisture absorbing agent, which is selected from calcium sulfate, calcium chloride, potassium chloride, any hydrates thereof, and any combination thereof.

Examples of the stabilizing agent include, but are not limited to, strontium chloride hexahydrate, NaCl, and any combination thereof. In some embodiments, the antimicrobial and/or photothermal agent may include, zinc oxide, titanium oxide, a combination thereof.

In some embodiments, the hydrogel may also include encapsulated dissolved alcohols such as xylitol. The hydrogel may also include dissolved salts such as $MgCl_2$ or $CaCl_2$.

In some embodiments, the base polymer in the hydrogel layer is polyacrylamide (PAM), the second base ingredient comprises a bisacrylamide as a crosslinker. In some preferred embodiments, the hydrogel layer has covalent crosslinks as a single type of crosslinking structure. In some other embodiments, the second base ingredient include an alginate, and the hydrogel layer has both covalent and ionic crosslinking structures.

In some embodiments, the base polymer in the hydrogel layer is a dual-network polyacrylamide (PAM), and the second base ingredient for the hydrogel layer is calcium alginate. In some embodiments, the base polymer in the hydrogel layer is a single-network polyacrylamide (PAM). The additive or filler comprises calcium chloride hexahydrate and calcium sulfate. The stabilizing agents comprise strontium chloride hexahydrate and NaCl.

The hydrogel layer comprises at least 50% of a liquid portion based on a total weight of the hydrogel layer. In some embodiments, the hydrogel layer comprises 80% to 86% of the liquid portion based on the total weight of the hydrogel layer.

In some embodiments, the backing layer comprises a bioplastic composite with additives. The backing layer is coated with a bioglue as the first adhesive layer and disposed on a first side of the hydrogel layer. The second adhesive layer is disposed on a second side of the hydrogel layer, and the second side being opposite to the first surface.

Examples of a suitable material for the backing layer include, but are not limited to, an alginate film, a cotton fabric, a bamboo fabric, a lyocell fabric, a cellulose film, a silicone foam, and a combination thereof. For example, in some embodiments, the protective backing layer is a bioplastic film comprising alginate and/or carboxymethylcellulose crosslinked by calcium chloride.

Examples of additives to the backing layer include, but are not limited to, kaolin clay, barium sulfate, calcium carbonate, zinc oxide, xanthan gum, and any combination thereof.

In some embodiments, the backing layer is a bioplastic composite comprising alginate and carboxymethylcellulose crosslinked by calcium chloride.

Examples of a suitable material for the first adhesive layer (i.e., glue layer) include, but are not limited to, chitosan, glycerin, and a combination thereof.

The second adhesive layer comprises an adhesive suitable for contacting skin of a subject such as a human being. Examples of a suitable adhesive include, but are not limited to, medical grade acrylic-based or silicone-based pressure sensitive adhesive, polyacrylic acid, thermoplastic hot melt adhesive, chitosan, polyallylamine, polyethylenimine, collagen, gelatin, and any combination thereof.

In some embodiments, the second adhesive layer comprises medical grade silicone-based pressure sensitive adhesive.

Each layer has any suitable thickness, for example, in a range of from 0.5 mm to 1 cm (e.g., from 1 mm to 10 mm).

In another aspect, the present disclosure provides a method of making the cooling pad as described herein. The method comprises steps of making each component and combining together to form the cooling pad. Such a method may comprise steps of forming the hydrogel layer, coating the first adhesive layer onto the protective backing layer, applying the protective backing layer coated with the first adhesive layer onto the first side of the hydrogel layer, and coating the second adhesive layer on the second side of the hydrogel layer.

In another aspect, the present disclosure provides a pack comprising an enclosure and the cooling pad enclosed therein. In the pack, the cooling pad may further comprise a release film disposed on the second adhesive layer.

The present disclosure provides a method of using the cooling pad as described herein.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

FIG. 7 shows the profiles of temperature versus time. FIG. 8 shows the temperature change versus time.

Figure 1:
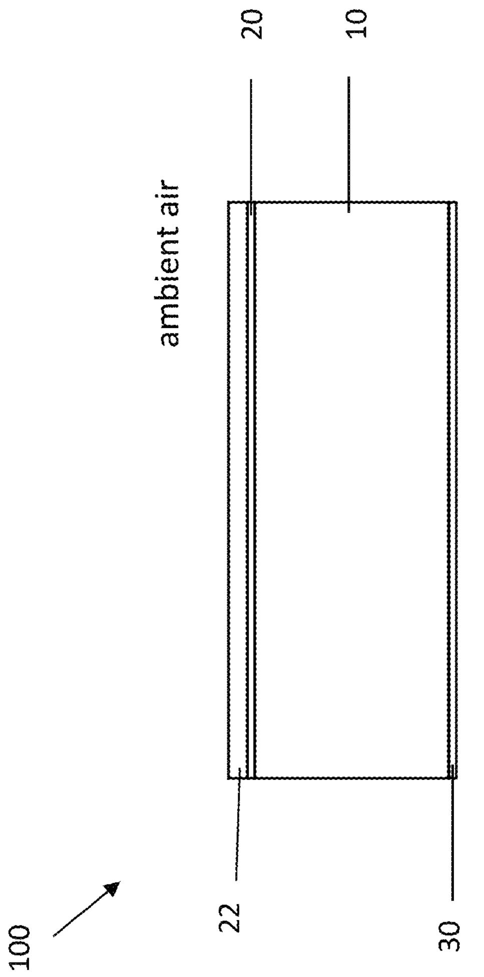
FIG. 1 is a sectional view illustrating an exemplary cooling pad in accordance with some embodiments.

Reference numerals: 100—exemplary cooling pad, 10—a hydrogel layer, 20—a first adhesive layer (or called glue layer), 30—a second adhesive layer, 22—a protective backing layer, 50—surface that the cooling pad is configured to contact, for example, skin of a subject such as a human being, 24—a main or middle portion of the cooling pad, 26—the edges of the cooling pad.

DETAILED DESCRIPTION

This description of the exemplary embodiments is intended to be read in connection with the accompanying drawings, which are to be considered part of the entire written description. In the description, relative terms such as “lower,” “upper,” “horizontal,” “vertical,”, “above,” “below,” “up,” “down,” “top” and “bottom” as well as derivative thereof (e.g., “horizontally,” “downwardly,” “upwardly,” etc.) should be construed to refer to the orientation as then described or as shown in the drawing under discussion. These relative terms are for convenience of description and do not require that the apparatus be constructed or operated in a particular orientation. Terms concerning attachments, coupling and the like, such as “connected” refer to a relationship wherein structures are secured or attached to one another either directly or indirectly through intervening structures, as well as both movable or rigid attachments or relationships, unless expressly described otherwise.

For purposes of the description hereinafter, it is to be understood that the embodiments described below may assume alternative variations and embodiments. It is also to be understood that the specific articles, compositions, and/or processes described herein are exemplary and should not be considered as limiting.

In the present disclosure, the singular forms "a," "an," and "the" include the plural reference, and reference to a particular numerical value includes at least that particular value, unless the context clearly indicates otherwise. Thus, for example, a reference to "a nano structure" is a reference to one or more of such structures and equivalents thereof known to those skilled in the art, and so forth. When values are expressed as approximations, by use of the antecedent "about," it will be understood that the particular value forms another embodiment. As used herein, "about X" (where X is a numerical value) preferably refers to +10% of the recited value, inclusive. For example, the phrase "about 8" preferably refers to a value of 7.2 to 8.8, inclusive; as another example, the phrase "about 8%" preferably (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

Unless expressly expressed otherwise, the percentages descried herein are weight percentages.

The term "hydrogel" used herein refers to a gel which includes a water-insoluble, three-dimensional network of polymer chains capable of holding large amounts of water. The polymer or polymers therein may include ionic, covalent or both ionic and covalent crosslinking structure. A compound comprising ions and/or a curative as a crosslinker may be used to form crosslinks in the polymer or polymers, which are generally hydrophilic. The hydrogel is highly absorbent and also has good mechanical properties.

The term "double network hydrogel" used herein refers to a hydrogel having two types of crosslinks, for example, both covalent and ionic crosslinks. Such a double network hydrogel has an interpenetrating network (IPN) structure.

The term "single network hydrogel," "mono-network hydrogel," or "singular network hydrogel" used herein refers to a hydrogel having only one single type of crosslinks, for example, covalent crosslinks only without ionic crosslinks. The hydrogel described in preferred embodiments in the present disclosure is a single network hydrogel.

In FIGS. 1-4, like items are indicated by like reference numerals, and for brevity, descriptions of the structure, provided above with reference to the preceding figures, are not repeated. The method in FIG. 5 is described with reference to the exemplary structure described in FIGS. 1-4.

The present disclosure provides a cooling pad (or patch), a pack comprising such a cooling pack, a method of making the cooling pad, and a method of using the cooling pad are provided.

The present disclosure provides a wearable personal cooling solution that harnesses passive cooling, more specifically, the dissipation of heat via evaporation of water out of a hydrogel. Hydrogel-based evaporative cooling mimics perspiration of mammals. The hydrogel in the cooling pad provided in the present disclosure also utilizes unique combination of polymer or polymers and additives and/or fillers.

Phase change materials (PCMs), which are similarly electricity-independent, have been used in personal cooling products, but PCMs are limited by their low latent heat (on the order of hundreds of kJ $kg^{-1}$) and their expensive material cost. For example, paraffin is one of the most common PCMs and costs $1692-1800/$m^3$ with a latent heat of 147 kJ $kg^{-1}$. PCMs also do not adhere to the human body, so PCM-based products impose an additional layer of clothing or necessitate a separate accessory for attachment. In comparison, alginate-polyacrylamide (PAM) hydrogel, which is one exemplary hydrogel used in the cooling pad in the present disclosure, costs about $370/$m^3$ and the latent heat of water vaporization is 2260 kJ $kg^{-1}$. The polyacrylamide hydrogel having a single type of network may cost even less while also having the same or similar latent heat of water vaporization.

In accordance with some embodiments, the cooling pad (or patch) provided in the present disclosure comprises four layers: a hydrogel layer, a backing layer that faces the ambient environment, and a first adhesive layer (or called a glue layer) that bonds the hydrogel and the backing layer, and a second adhesive layer. The second adhesive layer is disposed on the hydrogel layer and is configured to adhere to a surface such as human skin. When not in use, the patch is stored in a sealed insulating pouch to prevent dehydration of the hydrogel; it does not require refrigeration.

Figure 6:
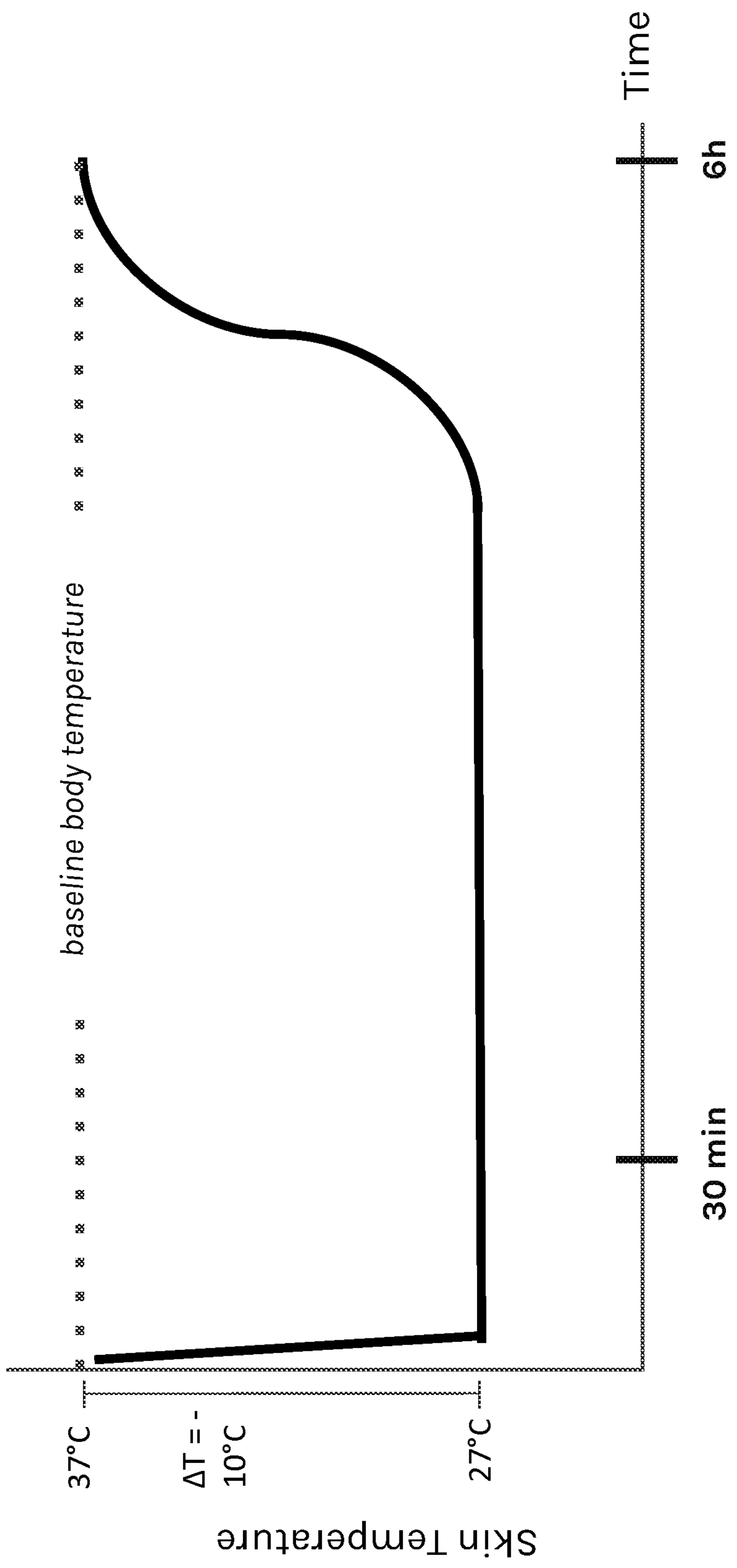
FIG. 6 illustrates the cooling effect on skin of an exemplary cooling pad provided in the present disclosure.

To use the cooling pad (or patch), one removes it from the packaging and presses the patch on one's body for adhesion. Upon contact with skin (temperature ~36° C.), water evaporates out of the hydrogel and into the ambient environment, effectively drawing heat away from the body and reducing skin temperature. For example, in the first 30 minutes of use, the patch achieves a temperature reduction of ~10° C. in the skin of contact (as illustrated in FIG. 6). The temperature reduction effect is sustained over time to provide safe cooling for a total of 6 hours until the hydrogel is dried out. To re-use the patch, one soaks it in water for a period of time, for example, about 30 minutes, to rehydrate the hydrogel. The cooling pad may also absorb moisture from air or in a moisture chamber for hydration during storage before reuse. The patch can then be placed on the human body for another cycle of cooling. The patch can be used for a plurality of times, for example, up to 20-25 cycles of cooling or a lifespan of one month from the time of first use, before it is disposed of due to wear and tear.

The cooling pad (or patch) provided in the present disclosure is thin, contours to the human body, and adheres well to a sweaty and dynamic skin surface. The hydrogel layer in contact with skin is biocompatible. The water-based nature of the material and its independence from refrigeration makes it particularly suitable for travel and places where power grid access is limited.

Referring to FIG. 1, a cooling pad (or patch) 100. Such a cooling pad 100 comprises a hydrogel layer 10, a first adhesive layer 20, a protective backing layer 22, and an adhesive layer 30. The backing layer 22 with glue (i.e., the first adhesive layer) and an adhesive layer 30 are disposed on two different sides of the hydrogel layer 10.

In some embodiments, the backing layer 22 comprises a fabric, a film or a foam, which is optionally surface treated on the exterior surface. The protective backing layer 22 and the first adhesive layer 20 are disposed on a first side of the hydrogel layer. The first adhesive layer 20 is disposed between the hydrogel layer 10 and the protective backing layer 22. The second adhesive layer 30 is disposed on a second side of the hydrogel layer. The second side is opposite to the first surface.

The hydrogel layer 10 comprises a solid gel portion and a liquid portion comprising water. The liquid portion is embedded and distributed within the solid gel portion. The solid gel portion of the hydrogel layer 10 comprises a base polymer as a first base ingredient for the hydrogel layer, moieties of a second base ingredient for the hydrogel layer, and an additive or filler. The second base ingredient is crosslinked or co-polymerized with the first base ingredient for the hydrogel layer 10. The additive or filler may include a moisture absorbing agent, a stabilizing agent, an antimicrobial agent, a photothermal agent, and any combination thereof.

The hydrogel layer 10 is configured to provide cooling. The hydrogel can be crosslinked, either chemically or physically. In some embodiments, the hydrogel is chemically crosslinked. During the synthesis of the hydrogel, a compound having ions such as cations (e.g., calcium ions) and/or a monomer curative used as a crosslinker can be used to form ionic and/or covalent crosslinks among the polymer chains.

Examples of the base polymer 10 in the hydrogel layer 10 include, but are not limited to, polyacrylamide (PAM), poly(N-isopropylacrylamide) (PNIPAM), polyvinyl alcohol (PVA), oligo(ethylene glycol) methacrylate (OEGMA), 2-(2-methoxyethoxy) ethyl methacrylate (MEO2MA), Xylan, carboxymethylcellulose sodium, and any combination thereof.

Examples of the second base ingredient for the hydrogel layer 10 include, but are not limited to, a bisacrylamide, calcium alginate, hyaluronic acid, 2-acrylamido-2-methylpropane sulfonic acid (AMPS), ethylene glycol-modified pillar[5]arene, and any combination thereof. The second base ingredient may include a crosslinker and a curatives for forming crosslinking structure or structures. One example is a bisacrylamide.

Examples of the additive or filler include, but are not limited to, $CaSO_4$, calcium chloride hexahydrate, LiCl, KCl, zinc oxide, $TiO_2$, carbon nanotube, $CaCl_2$, LiBr, $MgCl_2$, silica microsphere or nanosphere, antimony-tin oxide nanoparticle, graphene oxide, tungsten bronze nanorods, and any combination thereof. The fillers can be nanoparticle or microparticles. The filler can be thermally conductive, a desiccant, or a phase change material, and is not water soluble. Thermally conductive fillers increase the heating capacity of hydrogel. Other suitable conductive metals or ceramics may be used.

Sometimes the additive is water soluble. With water vapor solvents/sorbents, hygroscopic salts with high water affinity can be dissolved in hydrated hydrogel. For example, $CaCl_2$ and $MgCl_2$ are exothermic when dissolved, and could absorb heat during endothermic recrystallization when water evaporates out of the hydrogel.

In some embodiments, the hydrogel may also include encapsulated dissolved alcohols such as xylitol. The hydrogel may also include dissolved salts such as $MgCl_2$ or $CaCl_2$.

In some embodiments, the base polymer in the hydrogel layer 10 is polyacrylamide (PAM), and the second base ingredient for the hydrogel layer 10 is calcium alginate. In the calcium alginate-PAM hydrogel, a monomer curative such as N,N'-methylenebis(acrylamide) (MBAA) may be used as a crosslinker. A crosslinking accelerator and/or a photoinitiator may be used. The resulting hydrogel may include two types of crosslinking structures: ionic crosslinking by calcium ions in alginate, and a covalent crosslinking in PAM. The two types of systems are mixed together uniformly and form an interpenetrating network.

In some preferred embodiments, the hydrogel layer 10 comprises or is made of a single network of covalently crosslinked polyacrylamide. In such a hydrogel, a monomer curative, for example, a bisacrylamide such as N,N'-methylenebis(acrylamide) (MBAA), may be used as a crosslinker. A crosslinking accelerator and/or a photoinitiator may be used. No alginate such as calcium alginate is used. The additive or filler comprises calcium chloride hexahydrate. Calcium chloride hexahydrate is a preferred filler to be used because it is a phase change material as well as a hygroscopic salt. Such a hydrogel comprising a single network of covalently crosslinked polyacrylamide is preferred.

In some embodiments, the additive or filler comprises a moisture absorbing agent such as calcium sulfate, calcium chloride, potassium chloride, any hydrates thereof, and any combination thereof. In some embodiments, the additive or filler comprises a stabilizing agent selected from strontium chloride hexahydrate, NaCl, and any combination thereof. Examples of an antimicrobial agent include, but are not limited to zinc oxide, titanium oxide, and a combination thereof. Zinc oxide, titanium oxide, and a combination thereof can be also examples of a photothermal agent.

In the hydrogel formation, each ingredient may include a suitable range. For example, in some embodiments, by the total dry weight (i.e., in the solid gel portion), the base polymer as the first base ingredient for the hydrogel layer may be in a range of from 10-90 wt. %, for example, from 10% to 80%, from 10% to 70%, from 10% to 60%, from 10% to 50%, from 10% to 40%, from 10% to 30%, or any other suitable range. The second base ingredient for the hydrogel layer may be in the range of 10-90 wt. %, for example, from 10% to 80%, from 10% to 70%, from 10% to 60%, from 10% to 50%, from 10% to 40%, from 10% to 30%, or any other suitable range. The additive or filler may be in a range of 0.5-50 wt. %, for example, from 5% to 40%, from 10% to 40%, from 5% to 30%, from 10% to 30%, from 5% to 20%, from 10% to 20%, or any other suitable range. The crosslinker may be in a range from 0.1 wt. % to 10%, for example, 0.5 wt. % to 6 wt. %.

The hydrogel layer 10 comprises at least 50% of a liquid portion based on a total weight of the hydrogel layer. The hydrogel may include a high percentage of water, for example, in a range of from 50% to 95% by weight of the total hydrogel layer 10. In some embodiments, the hydrogel layer comprises 80% to 86% of the liquid portion based on the total weight of the hydrogel layer. For example, such water content may be 85%.

The hydrogel used may be transparent or translucent.

Carbon nanotubes including multi-walled or single-walled nanotubes may be used. The hydrogel containing carbon nanotubes may be black or light brown in color. A small percentage of CNTs such as single-walled CNTs may be dispersed well enough to make a transparent hydrogel.

The fillers used can be photothermal nanoheaters. For example, antimony-tin oxide (ATO) nanoparticles absorb near-infrared light. Zinc oxide can have double effects as a thermally conductive filler and a photothermal nanoheater. Zinc oxide can be used for a thermal effect i.e., heating. Graphene oxide and tungsten bronze nanorods (CsxWO3NRs) can be also used.

The hydrogel layer 10 has any suitable thickness, for example, in a range of from 0.5 mm to 1 cm (e.g., from 1 mm to 10 mm). In some embodiments, the hydrogel layer 10 is 5 mm thick. In some embodiments, the hydrogel layer 10 is a 5 mm-thick PAM hydrogel or calcium alginate/PAM hydrogel, with calcium sulfate and calcium chloride hexahydrate dispersed throughout the matrix.

Calcium alginate/PAM hydrogel provides cooling to a surface such as skin, and served as the dissipative matrix utilized in the invention of tough adhesives. Alginate is hygroscopic and improves the mechanical properties of the hydrogel. Zinc oxide is added to the matrix as a biocompatible, thermally conductive, and photothermal nanoheater. Heating of the hydrogel leads to evaporation of water out of the hydrogel and cooling of the underlying surface, which is human skin for the cooling patch or pad provided in the present disclosure. In some embodiments, the hydrogel is heated in two main ways: 1) body heat is transferred to the hydrogel via conduction, and 2) zinc oxide nanoparticles convert solar energy (ambient light) into thermal energy (local heat).

In accordance with some embodiments, a single network hydrogel is preferred. The solid gel portion comprises moieties of an acrylamide as a monomer, a bisacrylamide as a crosslinker, a moisture absorbing agent, and an antimicrobial agent. The liquid portion comprises water, and is water, a toning water, an essence water, or any combination thereof. The liquid portion is embedded and distributed within the solid gel portion. The hydrogel layer has covalent crosslinks as a single type of crosslinking structure. In some embodiments, no ionic crosslinks exist in the hydrogel layer.

The base polymer in the hydrogel layer is polyacrylamide (PAM). No other base ingredient such as alginates for a dual network hydrogel is used. The resulting hydrogel is a single network hydrogel.

The liquid portion comprising water may be in any amount even though at least 50% is preferred. The hydrogel may have less water and may be soaked in water to increase water content before use. For example, the content of the liquid portion may be in a range of 50%-95%, 50%-90%, 60%-95%, 70%-95%, or 80%-95%. In some embodiments, the hydrogel layer comprises 80% to 86% (e.g., 84-86%) of the liquid portion based on the weight of liquid portion in the total weight of the hydrogel.

The polyacrylamide hydrogel include additives such as calcium sulfate, calcium chloride, or potassium chloride as desiccants that enhance cooling performance; zinc oxide or titanium dioxide for antimicrobial and photothermal properties; and skincare toning or essence water for skincare benefits. Examples of a suitable moisture absorbing agent (or desiccator) include, but are not limited to, calcium sulfate, calcium chloride, potassium chloride, any hydrates thereof, and any combination thereof. Examples of a suitable antimicrobial agent include, but are not limited to zinc oxide, titanium oxide, and any combination thereof. The toning or essence water can be customized to confer different benefits and may comprise ingredients including, but not limited to, glycerin, agar, xanthan gum, carrageenan, carob gum, cellulose gum, hydrolyzed collagen, hyaluronic acid, potassium sorbate, sucrose, glucose, inositol, disodium EDTA, 1,2-hexanediol, allantoin, polyglyceryl-10 laurate, butylene glycol, dipropylene glycol, and any combination thereof.

In some embodiments, the solid gel portion comprises 50%-80% of the moieties of the acrylamide, 0.1%-1% of the moieties of the bisacrylamide, 0.1%-20% of the moisture absorbing agent, and 0.1%-25% of the antimicrobial agent, based on a total weight of the solid gel portion on a dry weight basis.

For example, the content of the moisture absorbing agent is in a range of 1%-18%, for example, 9%-18%, based on a total weight of the solid gel portion on a dry weight basis. The content of the antimicrobial agent may be in a range of 1%-25%, 1%-20%, 2%-25%, 5%-25%, or any other suitable ranges, based on a total weight of the solid gel portion on a dry weight basis.

In some embodiments, the solid gel portion further comprises moieties from an initiator in a range of from 1% to 8% (e.g., 3%-8%) and an accelerator in a range of from 0.1% to 1% (e.g., 0.1%-0.5%), based on a total weight of the solid gel portion on a dry weight basis. For example, in some embodiments, the initiator is ammonium persulfate (APS) and the curative and/or accelerator is N,N'-methylenebis (acrylamide) (MBAA).

In accordance with some embodiments, the hydrogel layer 10 in the cooling pad 100 comprises 50%-95% (e.g., 80%-86%) of a liquid portion based on a total weight of the hydrogel layer, and a solid gel portion. The solid gel portion consists essentially of moieties of an acrylamide as a monomer, a bisacrylamide as a crosslinker, an initiator, an accelerator, a moisture absorbing agent, and an antimicrobial agent. Each ingredient is described herein.

The monomer curative such as N,N'-methylenebis(acrylamide) (MBAA) may be used as a crosslinker. A crosslinking accelerator and/or a photoinitiator may be used.

In some embodiments, the solid gel portion comprises 50%-80% of the acrylamide, 0.1%-1% of the bisacrylamide, 1%-8% of the initiator, 0.1% to 1% of the accelerator, 0.1%-20% of the moisture absorbing agent, and 0.1%-25% of the antimicrobial agent, based on corresponding moieties and a total weight of the solid gel portion on a dry weight basis.

In some embodiments, the bisacrylamide such as N,N'-methylenebis(acrylamide) (MBAA) has a content of 0.1%-1% by weight, for example, 0.109%, 0.218%, 0.273%, and 0.327%, or any other suitable percentage.

In some embodiments, in the cooling pad, the acrylamide and the bisacrylamide provide the matrix of the hydrogel.

The hydrogel layer 10 is configured to provide directional evaporative cooling when the water inside the hydrogel layer 10 evaporates. Heat from a human body is dissipated via evaporation of water out of the hydrogel. Hydrogel-based evaporative cooling mimics perspiration of mammals. The hydrogel in the present disclosure also utilizes unique combination of polymer or polymers and additives and/or fillers.

The protective backing layer 22 is a bioplastic composite. Such a bioplastic layer may radiate heat to augment the cooling performance of the product in addition to evaporative cooling from the hydrogel layer. It is also thin to minimize its blockage of water evaporation from the hydrogel layer underneath. The backing layer may include additives that radiate or reflect heat, improve rehydration capacity, and improve texture into the bioplastic film.

Examples of a suitable material for the backing layer 22 include, but are not limited to, an alginate film, a cotton fabric, a bamboo fabric, a lyocell fabric, a cellulose film, a silicone foam, and a combination thereof.

The backing layer 22 may include one or more additives. Examples of suitable additives for the backing layer 22 include, but are not limited to, kaolin clay, barium sulfate, calcium carbonate, zinc oxide, xanthan gum, and any combination thereof.

In some embodiments, the backing layer 22 is a bioplastic composite comprising alginate and carboxymethylcellulose crosslinked by calcium chloride.

In some embodiments, the backing layer 22 is coated with a chitosan-glycerin bioglue (i.e., the first adhesive layer 20) for bonding to the hydrogel layer.

In some embodiments, the backing layer 22 is not coated. In some other embodiments, the exterior surface of the backing layer 22 is coated with a hydrophobic material or chemical. The hydrophobic chemical may be silane, siloxane or a fluorine containing chemical. Examples of a suitable hydrophobic chemical include, but are not limited to, trimethoxymethylsilane (MTMS), polydimethylsiloxane (PDMS), hexadecyltrimethoxysilane (HDTMS), dodecyltrietoxysilane (DTS), and any combination thereof.

The protective backing layer 22 has any suitable thickness, for example, in a range of from 0.5 mm to 1 cm (e.g., from 1 mm to 10 mm). In some embodiments, the backing layer 22 is 1 mm thick. In some embodiments, the backing is 1 mm-thick alginate-carboxymethylcellulose composite to make the product able to interface with clothing and the surrounding environment. Cellulose-based fibers such as carboxymethylcellulose can also reflect solar light and exhibit high infrared emissivity for radiative cooling.

The backing layer 22 is flexible and non-sticky because the product is a wearable patch meant to fit underneath clothing; this is different from the studies that utilize aerogels and other materials that are less extensible, flexible, and resistant to fatigue from dynamic movement, given that these inventions were geared towards cooling building infrastructure and not human individuals.

In some embodiments, a cotton fabric may be used as the backing layer 22, and the cotton fabric may be hydrophobized to confer water resistance on the wearable product.

The second adhesive layer 30 comprises an adhesive suitable for contacting skin of a subject such as a human being. The adhesive is biocompatible, reusable and sweat resistant. Examples of a suitable adhesive include, but are not limited to, a medical grade acrylic-based or silicone-based pressure sensitive adhesive, polyacrylic acid, thermoplastic hot melt adhesive, chitosan, polyallylamine, polyethylenimine, collagen, gelatin, and any combination thereof. In some embodiments, the second adhesive layer comprises a silicone pressure sensitive adhesive.

In some embodiments, similar to the first adhesive layer 20, the second adhesive layer 30 comprises chitosan. In some embodiments, both the first adhesive layer 20 and the second adhesive layer 30 comprise chitosan. For example, in some embodiments, chitosan of a suitable percentage, for example, in a range of from 0.1 wt. % to 3.0 wt. % is coated as an adhesive on the hydrogel surface. The weight percentage of chitosan is based on the total weight of a chitosan solution. For example, the percentage of chitosan may be in a range of from 0.1 wt. % to 0.5 wt. %, for example, 0.2 wt. %, 0.3 wt. %, 0.4 wt. %, or 0.5 wt. %. The adhesive layer 30 may have a thickness at micrometer level, for example, in a range of from 1 micron to 500 microns, from 5 microns to 200 microns, or from 10 microns to 100 microns, or any other suitable range. The adhesive may include bridging polymer with positively charged amine groups, in combination with a dissipative alginate-PAM hydrogel matrix.

Adhesive bandages typically have an adhesion energy in the range of 1-100 J $m^{-2}$ and matrix toughness on the order of several thousand to 10,000 J $m^{-2}$. Chitosan as an adhesive immediately can achieve an adhesion energy of ~250 J/$m^2$ upon attachment to biological tissue, and the adhesion energy reached 1000 J/$m^2$ by 30 minutes when compression is applied to the tissue samples for 5-30 minutes prior to mechanical testing. For the cooling pad provided in the present disclosure, compression is applied only momentarily upon the initial attachment of the patch to the user's body. In the context of minimal compression, it is estimated that the adhesion energy of the 0.3 wt % chitosan coating would be on the order of 250 J/$m^2$. The cooling pad or patch would be a stronger adhesive than existing adhesive bandages to withstand the dynamic movement and sweating of the human body, but it can still be easily peeled off.

In this invention, chitosan is used as a tough tissue adhesive for external application on a sweat-covered body under exercise activity.

The second adhesive layer 30 has any suitable thickness, for example, in a range of from 0.5 mm to 10 mm. In some embodiments, the second adhesive layer 30 is 0.5 mm or 1 mm thick.

Figure 2:
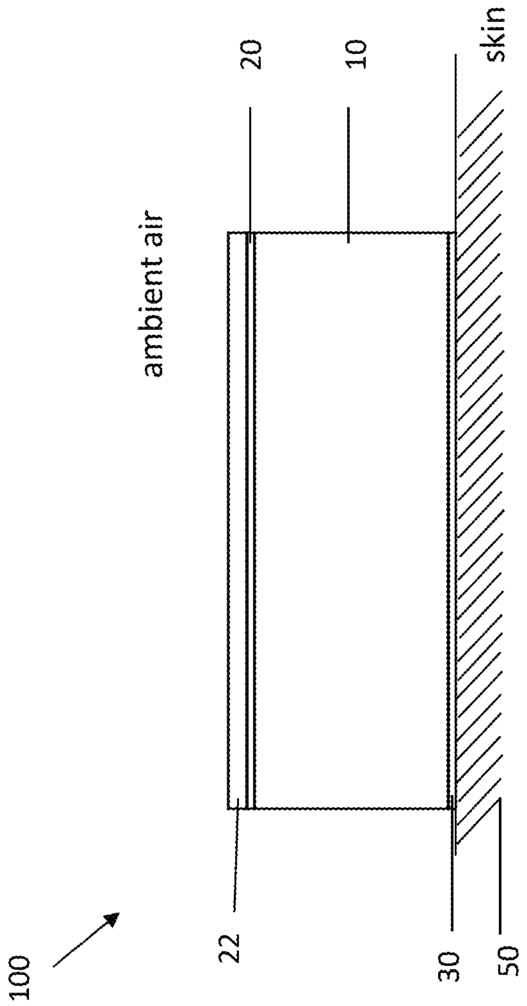
FIG. 2 is a sectional view illustrating the exemplary cooling pad of FIG. 1 disposed on a surface such as a skin.

Referring to FIG. 2, the exemplary cooling pad can be disposed on a surface 50 such as a skin. The surface 50 can be wet or dry. Before used, the cooling pad is stored in sealed packaging at room temperature. No refrigeration is needed. It can be peeled off and reused multiple times before disposal.

Figure 3:
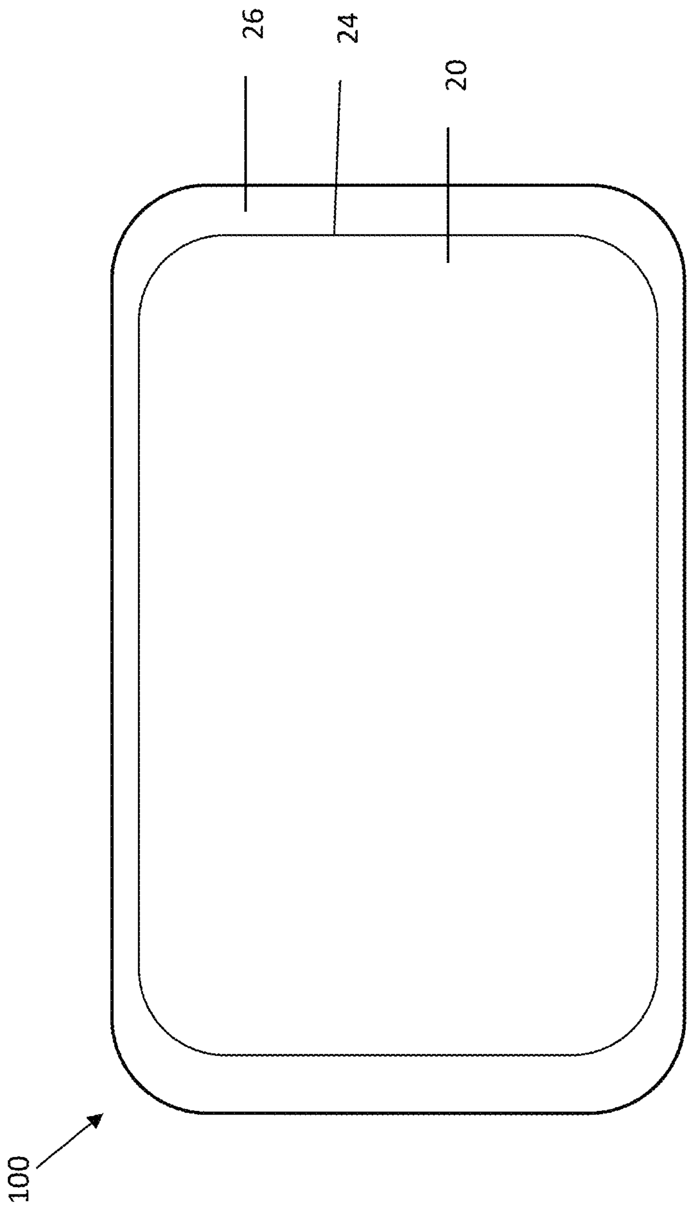
FIGS. 3-4 are plan views illustrating a front surface and a back surface of an exemplary cooling pad in accordance with some embodiments. The front surface and the back surface may include printed designs.
Figure 4:
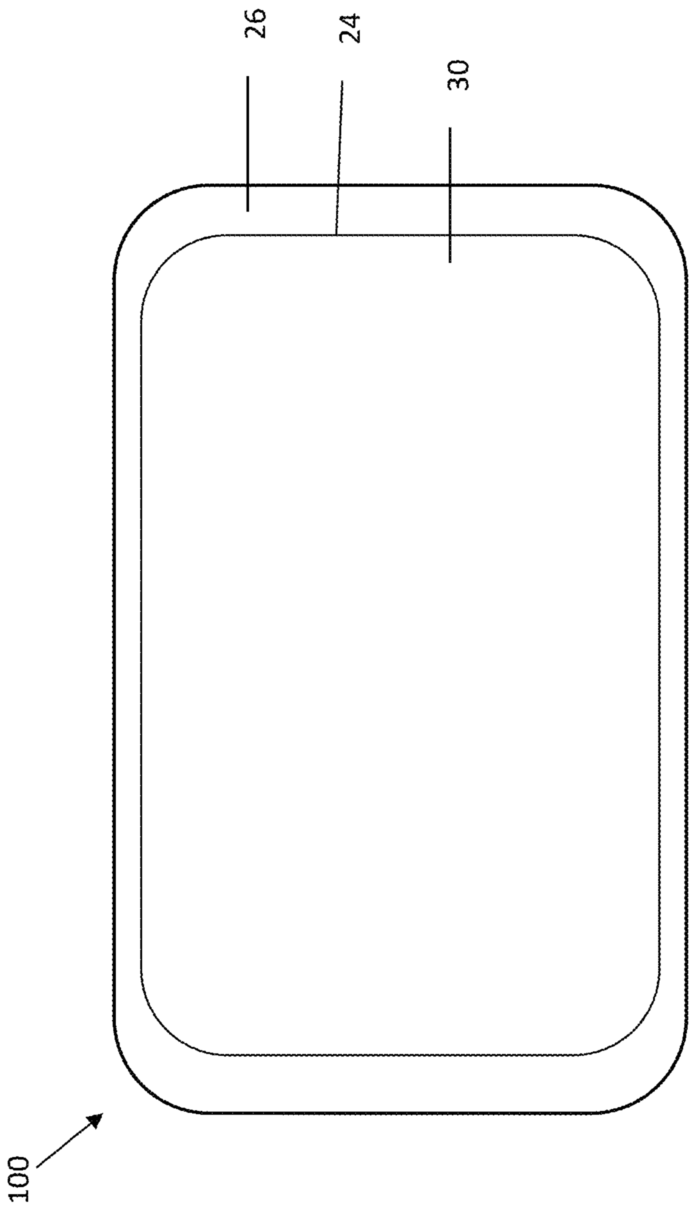
Figure 5:
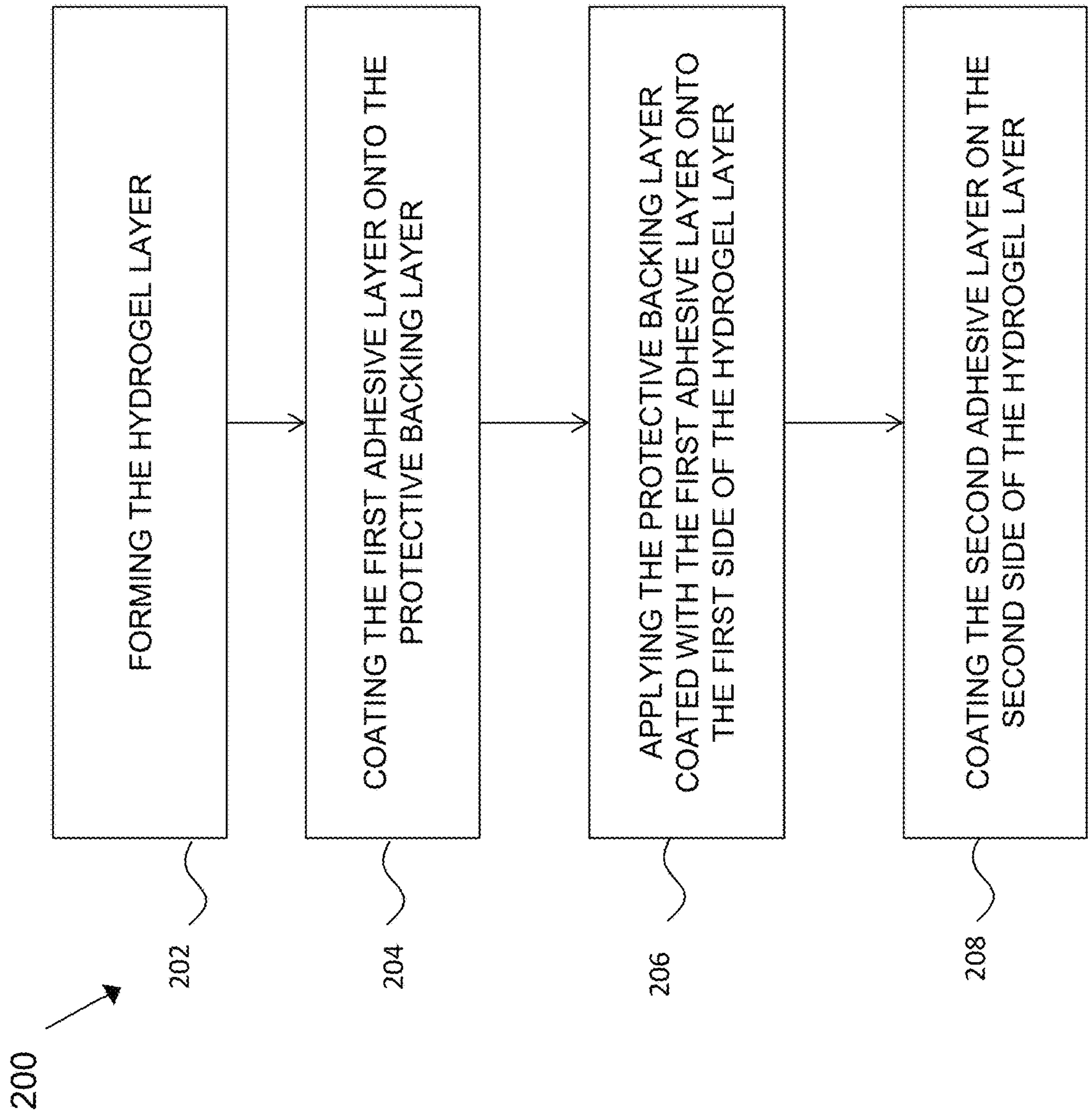
FIG. 5 is a flow chart illustrating an exemplary method of making the cooling pad in accordance with some embodiments.

Referring to FIGS. 3-4, a front surface and a back surface of an exemplary cooling pad are illustrated in accordance with some embodiments. The front surface and the back surface may include printed designs with colors. These are for illustration only. The cooling pad may be in any shape and at any size. For example, the cooling pad may be rectangular, square, circular, oval or any other regular or irregular shape.

In some embodiments, the cooling pad has a suitable thickness such as from 2 mm to 10 cm. In some embodiments the cooling pad has a thickness of 5 mm to 10 mm (e.g., 6 mm, 6.5 mm, 7 mm, 7.5 mm, 8 mm).

Referring to FIG. 5, an exemplary method 200 of making the cooling pad as described herein comprises the steps of making each component and combining together to form the cooling pad. Such a method comprises steps of making a hydrogel layer including making the formulation or the composition. In some embodiments, the method 200 may include steps 202, 204, 206, and 208.

At step 202, the hydrogel layer 10 is provided.

At step 204, the first adhesive layer 20 is coated onto the protective backing layer 22.

At step 206, the protective backing layer 22 coated with the first adhesive layer 20 is applied onto the first side of the hydrogel layer 10.

At step 208, the second adhesive layer 30 on the second side of the hydrogel layer 10. A release layer (not shown) may be added on one side of the second adhesive layer 30 so that it can be peeled and the second adhesive layer can be applied to a skin surface.

In some embodiments, forming the hydrogel layer comprises step or steps of mixing at least two portions of sols as described herein. The at least two portions of sols comprises a first portion of sol comprising the first base ingredient, and a second portion of sol comprises the second base ingredient. Each sol comprises water. In some embodiments, the first portion of sol comprises an acrylamide and the second portion of sol comprising a bisacrylamide.

In another aspect, the present disclosure provides a method of making the cooling pad as described herein. For example, such a method comprising at least one step of applying the cooling pad onto a surface such as skin or a body part of a subject. Such a subject is a human being, for example, an athlete or a patient.

The mechanism of action is directional evaporative cooling to mimic and augment sweating. Upon contact with human skins (or another warm surface), water evaporates out of the hydrogel matrix into the ambient environment, thus reducing the temperature of the skin in contact. The cooling effect ends when the hydrogel matrix is desiccated.

The material can be rehydrated with water or a composition for the liquid portion for a next cycle of cooling. The hydrogel material can withstand a plurality of cycles, such as 20 or 30 cycles of cooling prior to disposal. It can be stored at ambient temperature and atmosphere or a moisture chamber or a sealed insulating pouch or a closed container.

In another aspect, the present disclosure provides a pack comprising an enclosure and the cooling pad enclosed therein. In the pack, the cooling pad may further comprise a release film disposed on the second adhesive layer. The enclosure may be a bag made of a plastic or a metallized plastic film.

EXAMPLES

Preparation of Hydrogel Layer:

The samples below were prepared using the following procedures: Solution A (or sol A) and Solution B (or sol B) were mixed in 4:1 ratio by volume, and the desired volume of Solution C (or sol C) containing additives such as zinc oxide was added. The solutions were directly poured into closed molds of the desired shape of the cooling pad. Gelation occurred within 12 hours in the molds at room temperature. The hydrogel can then be removed from the mold for usage. The hydrogel had a thickness in a range of from 1 mm to 3 mm.

Sol A comprises acrylamide as the monomer in a range of 12.95-17.45 wt. % of Sol A (equivalent to 9-14.0 wt. % overall gel) and a liquid portion comprising water in a range of 82.5-87 wt. % of Sol A. The water portion is a deionized water. In some embodiments, the liquid portion is divided into skincare toning or essence water (0-28 wt. % overall gel) and deionized water (remaining water content in Sol A). In the formulations presented in Tables 1-12, "water" refers to the liquid portion comprising water including deionized water plus skincare toning or essence water. Sol A further includes TEMED of 0.05 wt. % of Sol A (equivalent to 0.03-0.04 wt. % overall gel).

Sol B comprises 0.109 wt. % N,N'-methylenebis(acrylamide) solution in a range of 22.5-31.4 wt % of Sol B (equivalent to 0.005-0.007 wt. % overall gel), 1.09 wt % ammonium persulfate solution in a range of 37.5-60 wt % of Sol B (equivalent to 0.08-0.11 wt % overall gel), and 6.06 wt % $CaSO_4 \frac{1}{2}H_2O$ solution in a range of 13.7-40 wt % of Sol B (equivalent to 0.15-0.48 wt % overall gel).

Sol C includes zinc oxide in a range of 0-5 wt % of total mass of the hydrogel product.

The water content in total in the overall gel ranges 84.3-89.1 wt % in the samples described herein.

Instruction to use the cooling pad includes the following exemplary procedures: the cooling pad is stored at room temperature in a closed container. The pad is then applied to the desired location on the body. After usage, the pad is soaked in water for rehydration, and is returned to its container for storage. The pad can be reused for another cycle of cooling after rehydration. The pad lasts for a number of cooling cycles, for example, 10, 20, or 30 cooling cycles, and can be used for one month before discarding.

Testing Methods: The testing conditions included controlled temperature chamber set at 37° C. and relative humidity 30-60%. Sample thickness was 2.5 mm. Samples were placed on temperature probes with data loggers on acrylic plates (acrylic model for human skin with similar thermal resistances). As illustrated in FIG. 6, the temperature drop (Δ) is a drop in temperature after sample placement, subtracted from temperature at t=0 (acrylic plate only). The plateau is the flat portion of the S-shaped temperature curve, after the initial temperature drop, during which the sample's cooling performance is relatively constant.

The formulations and experimental data of the hydrogel layers are shown in Tables 1-12. The results in Tables 1-12 were obtained from the hydrogel layers with one layer structure.

1. Effect of Alginate

Table 1 shows the formulations with and without alginate for forming double network and the related testing results. Sodium Alginate ("alg") was used. Table 2 shows the formulations excluding the water including skincare toning and essence water. Example 1 ("Ex. 1") can be considered as a comparative example. With a decreasing alginate content, gel toughness decreases and stickiness increases. Reducing the percentage of the alginate improves cooling magnitude and gel adhesion to skin. Therefore, in the cooling product provided in this disclosure, it is preferable not to use any alginate.

TABLE 1

| Formulation | Ex. 1 14.95 AAM/ 2.5 alg | Ex. 2 16.95 AAM/ 0.5 alg | Ex. 3 17.2 AAM/ 0.25 alg | Ex. 4 17.45 AAM/ 0 alg |
|---|---|---|---|---|
| Sol. A (by wt. % or part in Sol. A) | | | | |
| AAM | 14.95 | 16.95 | 17.2 | 17.45 |
| Sodium Alginate | 2.5 | 0.5 | 0.25 | 0 |
| Water | 82.5 | 82.5 | 82.5 | 82.5 |
| TEMED | 0.05 | 0.05 | 0.05 | 0.05 |
| Sol. A (% total gel) | 80 | 80 | 80 | 80 |
| Sol. B (by wt. % or part in Sol. B) | | | | |
| MBAA | 0.034 | 0.034 | 0.034 | 0.034 |
| Ammonium persulfate | 0.57 | 0.57 | 0.57 | 0.57 |
| $CaSO_4 \frac{1}{2}H_2O$ | 1 | 1 | 1 | 1 |
| Water | 98.4 | 98.4 | 98.4 | 98.4 |
| Sol. B (% total gel) | 20 | 20 | 20 | 20 |
| Overall Percentages in Gel | | | | |
| AAM | 12.0 | 13.6 | 13.8 | 14.0 |

TABLE 1-continued

| Formulation | Ex. 1 14.95 AAM/ 2.5 alg | Ex. 2 16.95 AAM/ 0.5 alg | Ex. 3 17.2 AAM/ 0.25 alg | Ex. 4 17.45 AAM/ 0 alg |
|---|---|---|---|---|
| Sodium Alginate | 2 | 0.4 | 0.2 | 0 |
| Water | 85.7 | 85.7 | 85.7 | 85.7 |
| TEMED | 0.04 | 0.04 | 0.04 | 0.04 |
| MBAA | 0.007 | 0.007 | 0.007 | 0.007 |
| Ammonium persulfate | 0.11 | 0.11 | 0.11 | 0.11 |
| $CaSO_4$ ½$H_2O$ | 0.20 | 0.20 | 0.20 | 0.20 |
| Properties | | | | |
| Max. Delta T (° C.) | 10.7 | 11.7 | 12.4 | 14.2 |
| Plateau Duration (mins) | 240 | 420 | 390 | 180 |
| Plateau Delta from Ambient (° C.) | 9 | 7 | 10 | 11.5 |
| Time to return to ambient temp(mins) | 480 | 660 | 780 | 330 |
| % Relative Humidity | 29 | 45 | 43 | 43 |
| Material Characterization | with decreasing alginate content, gel toughness decreases and stickiness increases | | | |

TABLE 2

| Formulation | Ex. 1 68 AAM/ 11 alg | Ex. 2 78 AAM/ 2 alg | Ex. 3 79 AAM/ 1 alg | Ex. 4 80 AAM/ 0 alg |
|---|---|---|---|---|
| Part A (by wt. % in Part A) | | | | |
| AAM | 85.4 | 96.9 | 98.3 | 99.7 |
| Sodium Alginate | 14.3 | 2.9 | 1.4 | 0.0 |
| TEMED | 0.3 | 0.3 | 0.3 | 0.3 |
| Part A (% total gel) | 80 | 80 | 80 | 80 |
| Part B (by wt. % in Part B) | | | | |
| MBAA | 2.1 | 2.1 | 2.1 | 2.1 |
| Ammonium persulfate | 35.5 | 35.5 | 35.5 | 35.5 |
| $CaSO_4$ ½$H_2O$ | 62.3 | 62.3 | 62.3 | 62.3 |
| Part B (% total gel) | 20 | 20 | 20 | 20 |
| Overall Percentages in Gel | | | | |
| AAM | 68.3 | 77.5 | 78.6 | 79.8 |
| Sodium Alginate | 11.4 | 2.3 | 1.1 | 0.0 |
| TEMED | 0.23 | 0.23 | 0.23 | 0.23 |
| MBAA | 0.42 | 0.42 | 0.42 | 0.42 |
| Ammonium persulfate | 7.1 | 7.1 | 7.1 | 7.1 |
| $CaSO_4$ ½$H_2O$ | 12.5 | 12.5 | 12.5 | 12.5 |

2. Effect of Monomer

Table 3 shows the formulations with different monomers such as acrylamide (AM) and N-isopropylacrylamide (NIPAM). Table 4 shows the formulations excluding the water including skincare toning and essence water. PNIPAM, as a thermoresponsive polymer, has a larger initial delta T than PAM but its cooling performance does not last as long. Double networks of PAM with PNIPAM or PAM with PVA exhibit a smaller cooling magnitude than PAM alone.

TABLE 3

| Formulation | Ex. 5 PAM | Ex. 6 PNIPAM | Ex. 7 PAM-PNIPAM | Ex. 8 PAM-PVA |
|---|---|---|---|---|
| Sol. A (by wt. % or part in Sol. A) | | | | |

TABLE 3-continued

| Formulation | Ex. 5 PAM | Ex. 6 PNIPAM | Ex. 7 PAM-PNIPAM | Ex. 8 PAM-PVA |
|---|---|---|---|---|
| AAM | 17.45 | 0 | 14.95 | 15.3 |
| NIPAM | 0 | 17.45 | 2.5 | 0 |
| Poly(vinyl) alcohol, hydrolyzed | 0 | 0 | 0 | 1.25 |
| Water | 82.5 | 82.5 | 82.5 | 83.4 |
| TEMED | 0.05 | 0.05 | 0.05 | 0.04 |
| Sol. A (% total gel) | 80 | 80 | 80 | 80 |
| Sol. B (by wt. % or part in Sol. B) | | | | |
| MBAA | 0.034 | 0.034 | 0.034 | 0.034 |
| Ammonium persulfate | 0.57 | 0.57 | 0.57 | 0.57 |
| $CaSO_4$ ½$H_2O$ | 1 | 1 | 1 | 1 |
| Water | 98.4 | 98.4 | 98.4 | 98.4 |
| Sol. B (% total gel) | 20 | 20 | 20 | 20 |
| Overall Percentages in Gel | | | | |
| AAM | 14.0 | 0.0 | 12.0 | 12.2 |
| NIPAM | 0 | 14.0 | 2 | 0 |
| Poly(vinyl) alcohol, hydrolyzed | 0 | 0 | 0 | 1 |
| Water | 85.7 | 85.7 | 85.7 | 86.4 |
| TEMED | 0.04 | 0.04 | 0.04 | 0.04 |
| MBAA | 0.007 | 0.007 | 0.007 | 0.007 |
| Ammonium persulfate | 0.11 | 0.11 | 0.11 | 0.11 |
| $CaSO_4$ ½$H_2O$ | 0.20 | 0.20 | 0.20 | 0.20 |
| Properties | | | | |
| Max. Delta T (° C.) | 12.3 | 13.1 | 10.2 | 11.1 |
| Plateau Duration (mins) | 210 | | 120 | 330 |
| Plateau Delta from Ambient (° C.) | 9 | No plateau | 9.5 | 9.5 |
| Time to return to ambient temp(mins) | 660 | | | 660 |
| % Relative Humidity | 51 | 53 | 50 | 51 |
| Material Characterization | | film not fully solidified | | |

TABLE 4

| Formulation | Ex. 5 PAM | Ex. 6 PNIPAM | Ex. 7 PAM-PNIPAM | Ex. 8 PAM-PVA |
|---|---|---|---|---|
| Part A (by wt. % in Part A) | | | | |
| AAM | 99.7 | 0.0 | 85.4 | 92.2 |
| NIPAM | 0.0 | 99.7 | 14.3 | 0.0 |
| Poly(vinyl) alcohol, hydrolyzed | 0.0 | 0.0 | 0.0 | 7.5 |
| TEMED | 0.3 | 0.3 | 0.3 | 0.3 |
| Part A (% total gel) | 80 | 80 | 80 | 80 |
| Part B (by wt. % in Part B) | | | | |
| MBAA | 2.1 | 2.1 | 2.1 | 2.1 |
| Ammonium persulfate | 35.5 | 35.5 | 35.5 | 35.5 |
| $CaSO_4$ ½$H_2O$ | 62.3 | 62.3 | 62.3 | 62.3 |
| Part B (% total gel) | 20 | 20 | 20 | 20 |
| Overall Percentages in Gel | | | | |
| AAM | 79.8 | 0.0 | 68.3 | 73.8 |
| NIPAM | 0.0 | 79.8 | 11.4 | 0.0 |
| Poly(vinyl) alcohol, hydrolyzed | 0.0 | 0.0 | 0.0 | 6.0 |
| TEMED | 0.23 | 0.23 | 0.23 | 0.21 |
| MBAA | 0.42 | 0.42 | 0.42 | 0.42 |
| Ammonium persulfate | 7.1 | 7.1 | 7.1 | 7.1 |
| $CaSO_4$ ½$H_2O$ | 12.5 | 12.5 | 12.5 | 12.5 |

3. Effect of Moisture Absorbing Agent

Table 5 shows the formulations with different levels of calcium sulfate as a moisture absorbing agent. Table 6 shows the formulations excluding the water including skincare toning and essence water. Increasing $CaSO_4$ content increases cooling magnitude and gel adhesion to skin, up to a certain level. However, with the content of calcium sulfate above a certain level, the cooling duration decreases. Up to 15% of the concentration of $CaSO_4$ by the dry weight of the gel portion, cooling duration increases with an increase in the concentration of $CaSO_4$; past 15% of the concentration of $CaSO_4$, cooling duration decreases as the concentration of $CaSO_4$ further increases.

TABLE 5

| Formulation | Ex. 9 82.5% water - 1 $CaSO_4$ | Ex. 10 82.5% water - 1.2 $CaSO_4$ | Ex. 11 85% water - 1.8 $CaSO_4$ | Ex. 12 85% water - 2.1 $CaSO_4$ | Ex. 13 85% water - 2.4 $CaSO_4$ |
|---|---|---|---|---|---|
| Sol. A (by wt. % or part in Sol. A) | | | | | |
| AAM | 17.45 | 17.45 | 14.95 | 14.95 | 14.95 |
| Water | 82.5 | 82.5 | 85 | 85 | 85 |
| TEMED | 0.05 | 0.05 | 0.05 | 0.05 | 0.05 |
| Sol. A (% total gel) | 80 | 80 | 80 | 80 | 80 |
| Sol. B (by wt. % or part in Sol. B) | | | | | |
| MBAA | 0.034 | 0.033 | 0.029 | 0.027 | 0.025 |
| Ammonium persulfate | 0.57 | 0.55 | 0.48 | 0.48 | 0.41 |
| $CaSO_4$ ½$H_2O$ | 1 | 1.2 | 1.8 | 2.1 | 2.4 |
| Water | 98.4 | 98.2 | 97.7 | 97.4 | 97.2 |
| Sol. B (% total gel) | 20 | 20 | 20 | 20 | 20 |
| Overall Percentages in Gel | | | | | |
| AAM | 14.0 | 14.0 | 12.0 | 12.0 | 12.0 |
| Water | 85.7 | 85.6 | 87.5 | 87.5 | 87.4 |
| TEMED | 0.04 | 0.04 | 0.04 | 0.04 | 0.04 |
| MBAA | 0.007 | 0.007 | 0.006 | 0.005 | 0.005 |
| Ammonium persulfate | 0.11 | 0.11 | 0.10 | 0.10 | 0.08 |
| $CaSO_4$ ½$H_2O$ | 0.20 | 0.24 | 0.36 | 0.42 | 0.48 |
| Properties | | | | | |
| Max. Delta T (° C.) | 12 | 12.7 | 10.7 | 10.3 | 11.7 |
| Plateau Duration (mins) | 120 | 150 | 360 | 270 | 240 |
| Plateau Delta from Ambient (° C.) | 9 | 10 | 9 | 9 | 10 |
| Time to return to ambient temp(mins) | 540 | 540 | 660 | 690 | 660 |
| % Relative Humidity | 53 | 53 | 61 | 59 | 61 |
| Material Characterization | | Increasing $CaSO_4$ increases the gel stickiness | | | |

TABLE 6

| Formulation | Ex. 9 12.5 $CaSO_4$ | Ex. 10 13.5 $CaSO_4$ | Ex. 11 15.6 $CaSO_4$ | Ex. 12 16.1 $CaSO_4$ | Ex. 13 16.9 $CaSO_4$ |
|---|---|---|---|---|---|
| Part A (by wt. % in Part A) | | | | | |
| AAM | 99.71 | 99.71 | 99.67 | 99.67 | 99.67 |
| TEMED | 0.29 | 0.29 | 0.33 | 0.33 | 0.33 |
| Part A (% total gel) | 80 | 80 | 80 | 80 | 80 |
| Part B (by wt. % in Part B) | | | | | |
| MBAA | 2.1 | 1.9 | 1.3 | 1.0 | 0.9 |
| Ammonium persulfate | 35.5 | 30.8 | 20.8 | 18.4 | 14.5 |
| $CaSO_4$ ½$H_2O$ | 62.3 | 67.3 | 78.0 | 80.6 | 84.7 |
| Part B (% total gel) | 20 | 20 | 20 | 20 | 20 |
| Overall Percentages in Gel | | | | | |
| AAM | 79.8 | 79.8 | 79.7 | 79.7 | 79.7 |
| TEMED | 0.23 | 0.23 | 0.27 | 0.27 | 0.27 |
| MBAA | 0.42 | 0.37 | 0.25 | 0.21 | 0.18 |
| Ammonium persulfate | 7.1 | 6.2 | 4.2 | 3.7 | 2.9 |
| $CaSO_4$ ½$H_2O$ | 12.5 | 13.5 | 15.6 | 16.1 | 16.9 |

4. Effect of Antimicrobial Agent

Table 7 shows the formulations with different levels of zinc oxide as an antimicrobial agent. Table 8 shows the formulations excluding the water portion including skincare toning and essence water. Adding zinc oxide does not compromise cooling performance. Adding ZnO to 2 wt. % in total of the gel increases gel stiffness; past a certain saturation point, for example, with 5 wt. % ZnO in total of the gel (corresponding to 25% ZnO in the solid gel portion on dry weight basis), decreases gel integrity.

TABLE 7

| Formulation | Ex. 1 14.95 AAM/ 2.5 alg | Ex. 14 14.95 AAM/ 2.5 alg/ 1% ZnO | Ex. 15 14.95 AAM/ 2.5 alg/ 2% ZnO | Ex. 16 14.95 AAM/ 2.5 alg/ 5% ZnO |
|---|---|---|---|---|
| Sol. A (by wt. % in Sol. A) | | | | |
| AAM | 14.95 | 14.95 | 14.95 | 14.95 |
| Sodium Alginate | 2.5 | 2.5 | 2.5 | 2.5 |
| Water | 82.5 | 82.5 | 82.5 | 82.5 |
| TEMED | 0.05 | 0.05 | 0.05 | 0.05 |
| Sol. A (% total gel) | 80 | 76 | 72 | 60 |
| Sol. B (by wt. % in Sol. B) | | | | |
| MBAA | 0.034 | 0.034 | 0.034 | 0.034 |
| Ammonium persulfate | 0.57 | 0.57 | 0.57 | 0.57 |
| $CaSO_4$ ½$H_2O$ | 1 | 1 | 1 | 1 |
| Water | 98.4 | 98.4 | 98.4 | 98.4 |
| Sol. B (% total gel) | 20 | 19 | 18 | 15 |
| Sol. C (by wt. % in Sol. C) | | | | |
| Zinc oxide | | 20 | 20 | 20 |
| Water | | 80 | 80 | 80 |
| Sol. C (% total gel) | 0 | 5 | 10 | 25 |
| Overall Percentages in Gel | | | | |
| AAM | 12.0 | 11.4 | 10.8 | 9.0 |
| Sodium Alginate | 2 | 1.9 | 1.8 | 1.5 |
| Water | 85.7 | 85.4 | 85.1 | 84.3 |
| TEMED | 0.04 | 0.04 | 0.04 | 0.03 |
| Zinc oxide | 0 | 1 | 2 | 5 |
| MBAA | 0.007 | 0.006 | 0.006 | 0.005 |
| Ammonium persulfate | 0.11 | 0.11 | 0.10 | 0.09 |
| $CaSO_4$ ½$H_2O$ | 0.20 | 0.19 | 0.18 | 0.15 |
| Properties | | | | |
| Max. Delta T (° C.) | 10.7 | 10.9 | 10.9 | 10.7 |
| Plateau Duration (mins) | 240 | 480 | 180 | |
| Plateau Delta from Ambient (° C.) | 9 | 7.5 | 9.5 | 7 |
| Time to return to ambient temp(mins) | 480 | 660 | 450 | |

TABLE 7-continued

| Formulation | Ex. 1 14.95 AAM/ 2.5 alg | Ex. 14 14.95 AAM/ 2.5 alg/ 1% ZnO | Ex. 15 14.95 AAM/ 2.5 alg/ 2% ZnO | Ex. 16 14.95 AAM/ 2.5 alg/ 5% ZnO |
|---|---|---|---|---|
| % Relative Humidity | 29 | 43 | 29.5 | 34 |
| Material Characterization | | | white color, chalky, stiffer than 0% ZnO | very sticky, less integrity |

TABLE 8

| Formulation | Ex. 1 0 ZnO | Ex. 14 5 ZnO | Ex. 15 10 ZnO | Ex. 16 25 ZnO |
|---|---|---|---|---|
| Part A (by wt. % in Part A) | | | | |
| AAM | 85.4 | 85.4 | 85.4 | 85.4 |
| Sodium Alginate | 14.3 | 14.3 | 14.3 | 14.3 |
| TEMED | 0.3 | 0.3 | 0.3 | 0.3 |
| Part A (% total gel) | 80 | 76 | 72 | 60 |
| Part B (by wt. % in Part B) | | | | |
| MBAA | 2.1 | 2.1 | 2.1 | 2.1 |
| Ammonium persulfate | 35.5 | 35.5 | 35.5 | 35.5 |
| $CaSO_4$ ½$H_2O$ | 62.3 | 62.3 | 62.3 | 62.3 |
| Part B (% total gel) | 20 | 19 | 18 | 15 |
| Part C (by wt. % in Part C) | | | | |
| Zinc oxide | | 100 | 100 | 100 |
| Part C (% total gel) | 0 | 5 | 10 | 25 |

TABLE 8-continued

| Formulation | Ex. 1 0 ZnO | Ex. 14 5 ZnO | Ex. 15 10 ZnO | Ex. 16 25 ZnO |
|---|---|---|---|---|
| Overall Percentages in Gel | | | | |
| AAM | 68.3 | 64.9 | 61.5 | 51.3 |
| Sodium Alginate | 11.4 | 10.9 | 10.3 | 8.6 |
| TEMED | 0.23 | 0.22 | 0.21 | 0.17 |
| Zinc oxide | 0 | 5 | 10 | 25 |
| MBAA | 0.42 | 0.40 | 0.38 | 0.32 |
| Ammonium persulfate | 7.1 | 6.8 | 6.4 | 5.3 |
| $CaSO_4$ ½$H_2O$ | 12.5 | 11.8 | 11.2 | 9.4 |

5. Effect of Water

Table 9 shows the formulations with different "water" content, i.e., the content of the liquid portion comprising water. Table 10 shows the formulations excluding the water including skincare toning and essence water. Increasing water content up to 86% (in Sol A) increases cooling magnitude. When the water content is above 86%, cooling magnitude decreases. Increasing water content decreases gel integrity and increases gel stickiness and adhesion to skin.

TABLE 9

| Formulation | Ex. 17 82.5% water-16.3 $CaSO_4$ | Ex. 18 83.5% water-16.3 $CaSO_4$ | Ex. 19 85% water-16.3 $CaSO_4$ | Ex. 20 85% water-30 $CaSO_4$ | Ex. 21 86% water-30 $CaSO_4$ | Ex. 22 87% water-30 $CaSO_4$ |
|---|---|---|---|---|---|---|
| Sol. A (by wt. % or part in Sol. A) | | | | | | |
| AAM | 17.45 | 16.45 | 14.95 | 14.95 | 13.95 | 12.95 |
| Water | 82.5 | 83.5 | 85 | 85 | 86 | 87 |
| TEMED | 0.05 | 0.05 | 0.05 | 0.05 | 0.05 | 0.05 |
| Sol. A (% total gel) | 80 | 80 | 80 | 80 | 80 | 80 |
| Sol. B (by wt. % or part in Sol. B) | | | | | | |
| MBAA | 0.034 | 0.034 | 0.034 | 0.029 | 0.029 | 0.029 |
| Ammonium persulfate | 0.57 | 0.57 | 0.57 | 0.48 | 0.48 | 0.48 |
| $CaSO_4$ 1/2$H_2O$ | 1 | 1 | 1 | 1.8 | 1.8 | 1.8 |
| Water | 98.4 | 98.4 | 98.4 | 97.7 | 97.7 | 97.7 |
| Sol. B (% total gel) | 20 | 20 | 20 | 20 | 20 | 20 |
| Overall Percentages in Gel | | | | | | |
| AAM | 14.0 | 13.2 | 12.0 | 12.0 | 11.2 | 10.4 |
| Water | 85.7 | 86.5 | 87.7 | 87.5 | 88.3 | 89.1 |
| TEMED | 0.04 | 0.04 | 0.04 | 0.04 | 0.04 | 0.04 |
| MBAA | 0.007 | 0.007 | 0.007 | 0.006 | 0.006 | 0.006 |
| Ammonium persulfate | 0.11 | 0.11 | 0.11 | 0.10 | 0.10 | 0.10 |
| $CaSO_4$ 1/2$H_2O$ | 0.20 | 0.20 | 0.20 | 0.36 | 0.36 | 0.36 |
| Properties | | | | | | |
| Max. Delta T (° C.) | 12 | 11.6 | 13.2 | 10.9 | 11.2 | 10.3 |
| Plateau Duration (mins) | 120 | 330 | 150 | 330 | 330 | 300 |
| Plateau Delta from | 9 | 10 | 11.5 | 9 | 10 | 9 |

TABLE 9-continued

| Formulation | Ex. 17 82.5% water- 16.3 $CaSO_4$ | Ex. 18 83.5% water- 16.3 $CaSO_4$ | Ex. 19 85% water- 16.3 $CaSO_4$ | Ex. 20 85% water- 30 $CaSO_4$ | Ex. 21 86% water- 30 $CaSO_4$ | Ex. 22 87% water- 30 $CaSO_4$ |
|---|---|---|---|---|---|---|
| Ambient (° C.) | | | | | | |
| Time to return to ambient temp(mins) | 540 | 660 | 330 | 540 | 660 | |
| % Relative Humidity | 53 | 55 | 55 | 54 | 54 | 60 |
| Material Characterization | Increasing water content decreases gel toughness | | | | | |

TABLE 10

| Formulation | Ex. 17 82.5% water- 12.5 $CaSO_4$ | Ex. 18 83.5% water- 12.5 $CaSO_4$ | Ex. 19 85% water- 12.5 $CaSO_4$ | Ex. 20 85% water- 15.6 $CaSO_4$ | Ex. 21 86% water- 15.6 $CaSO_4$ | Ex. 22 87% water- 15.6 $CaSO_4$ |
|---|---|---|---|---|---|---|
| Part A (by wt. % in Part A) | | | | | | |
| AAM | 99.71 | 99.70 | 99.67 | 99.67 | 99.64 | 99.62 |
| TEMED | 0.29 | 0.30 | 0.33 | 0.33 | 0.36 | 0.38 |
| Part A (% total gel) | 80 | 80 | 80 | 80 | 80 | 80 |
| Part B (by wt. % in Part B) | | | | | | |
| MBAA | 2.1 | 2.1 | 2.1 | 1.3 | 1.3 | 1.3 |
| Ammonium persulfate | 35.5 | 35.5 | 35.5 | 20.8 | 20.8 | 20.8 |
| $CaSO_4$ $1/2H_2O$ | 62.3 | 62.3 | 62.3 | 78.0 | 78.0 | 78.0 |
| Part B (% total gel) | 20 | 20 | 20 | 20 | 20 | 20 |

TABLE 10-continued

| Formulation | Ex. 17 82.5% water- 12.5 $CaSO_4$ | Ex. 18 83.5% water- 12.5 $CaSO_4$ | Ex. 19 85% water- 12.5 $CaSO_4$ | Ex. 20 85% water- 15.6 $CaSO_4$ | Ex. 21 86% water- 15.6 $CaSO_4$ | Ex. 22 87% water- 15.6 $CaSO_4$ |
|---|---|---|---|---|---|---|
| Overall Percentages in Gel | | | | | | |
| AAM | 79.8 | 79.8 | 79.7 | 79.7 | 79.7 | 79.7 |
| TEMED | 0.23 | 0.24 | 0.27 | 0.27 | 0.29 | 0.31 |
| MBAA | 0.42 | 0.42 | 0.42 | 0.25 | 0.25 | 0.25 |
| Ammonium persulfate | 7.1 | 7.1 | 7.1 | 4.2 | 4.2 | 4.2 |
| $CaSO_4$ $1/2H_2O$ | 12.5 | 12.5 | 12.5 | 15.6 | 15.6 | 15.6 |

6. Effect of Toner

Table 11 shows the formulations with different levels of skincare toner solution. Table 12 shows the formulations excluding the water including skincare toning and essence water. Adding skincare toner decreases gel toughness. However, there is no observed decrease in cooling performance.

TABLE 11

| Formulation | Ex. 23 82.5% water- 16.3 $CaSO_4$ | Ex. 24 82.5% water- 16.3 $CaSO_4$- 28% toner | Ex. 25 85% water- 35 $CaSO_4$ | Ex. 26 85% water- 35 $CaSO_4$- 5% toner |
|---|---|---|---|---|
| Sol. A (by wt. % or part in Sol. A) | | | | |
| AAM | 17.45 | 17.45 | 14.95 | 14.95 |
| Water | 82.5 | 47.5 | 85 | 78.75 |
| Skincare Toner | 0 | 35 | 0 | 6.25 |
| TEMED | 0.05 | 0.05 | 0.05 | 0.05 |
| Sol. A (% total gel) | 80 | 80 | 80 | 80 |
| Sol. B (by wt. % or part in Sol. B) | | | | |
| MBAA | 0.034 | 0.034 | 0.027 | 0.027 |
| Ammonium persulfate | 0.57 | 0.57 | 0.48 | 0.48 |
| $CaSO_4$ $½H_2O$ | 1 | 1 | 2.1 | 2.1 |
| Water | 98.4 | 98.4 | 97.4 | 97.4 |
| Sol. B (% total gel) | 20 | 20 | 20 | 20 |
| Overall Percentages in Gel | | | | |
| AAM | 14.0 | 14.0 | 12.0 | 12.0 |
| Water | 85.7 | 57.7 | 87.5 | 82.5 |
| Skincare toner | 0 | 28 | 0 | 5 |
| TEMED | 0.04 | 0.04 | 0.04 | 0.04 |
| MBAA | 0.007 | 0.007 | 0.005 | 0.005 |
| Ammonium persulfate | 0.11 | 0.11 | 0.10 | 0.10 |
| $CaSO_4$ $½H_2O$ | 0.20 | 0.20 | 0.42 | 0.42 |

TABLE 11-continued

| Formulation | Ex. 23 82.5% water- 16.3 $CaSO_4$ | Ex. 24 82.5% water- 16.3 $CaSO_4$- 28% toner | Ex. 25 85% water- 35 $CaSO_4$ | Ex. 26 85% water- 35 $CaSO_4$- 5% toner |
|---|---|---|---|---|
| Properties | | | | |
| Max. Delta T (° C.) | 10.6 | 12.9 | 12.9 | 12.0 |
| Plateau Duration (mins) | >120 (time_final = 120) | 60 | 120 | 120 |
| Plateau Delta from Ambient (° C.) | 9.5 | 12.5 | 12.5 | 11.5 |
| Time to return to ambient temp(mins) | | | | |
| % Relative Humidity | 54 | 54 | 45 | 45 |
| Material Characterization | Increasing skincare toner content decreases gel toughness | | | |

TABLE 12

| Formulation | Ex. 23 12.5 $CaSO_4$ | Ex. 24 12.5 $CaSO_4$- 53% toner | Ex. 25 16.1 $CaSO_4$ | Ex. 26 16.1 $CaSO_4$- 24% toner |
|---|---|---|---|---|
| Part A (by wt. % in Part A) | | | | |
| AAM | 99.7 | 33.2 | 99.7 | 70.4 |
| Skincare Toner | 0 | 67 | 0 | 29 |
| TEMED | 0.29 | 0.10 | 0.33 | 0.24 |
| Part A (% total gel) | 80 | 80 | 80 | 80 |
| Part B (by wt. % in Part B) | | | | |
| MBAA | 2.1 | 2.1 | 1.0 | 1.0 |
| Ammonium persulfate | 35.5 | 35.5 | 18.4 | 18.4 |
| $CaSO_4$ ½$H_2O$ | 62.3 | 62.3 | 80.6 | 80.6 |
| Part B (% total gel) | 20 | 20 | 20 | 20 |
| Overall Percentages in Gel | | | | |
| AAM | 79.8 | 26.6 | 79.7 | 56.3 |
| Skincare toner | 0 | 53 | 0 | 24 |
| TEMED | 0.23 | 0.08 | 0.27 | 0.19 |
| MBAA | 0.42 | 0.42 | 0.21 | 0.21 |
| Ammonium persulfate | 7.1 | 7.1 | 3.7 | 3.7 |
| $CaSO_4$ ½$H_2O$ | 12.5 | 12.5 | 16.1 | 16.1 |

FIG. 6 illustrates the cooling effect of an exemplary cooling pad provided in the present disclosure. The cooling pad provides surprisingly good cooling performance, for example, decreasing skin temperature by 10 or 15 degrees C.

The mechanism of action is directional evaporative cooling to mimic and augment sweating. Upon contact with human skins (or another warm surface), water evaporates out of the hydrogel matrix and through the protective backing layer into the ambient environment, thus reducing the temperature of the skin in contact. The cooling effect ends when the hydrogel matrix is desiccated. The material can be rehydrated with water for a next cycle of cooling. The hydrogel material can withstand a plurality of cycles, such as 3-30 cycles of cooling prior to disposal. The material requires no activation other than coming in contact with the human body. It can be stored at ambient temperature and atmosphere or a moisture chamber or a sealed insulating pouch.

Exemplary cooling pads comprising a four-layer structure (FIG. 1) were prepared as follows. The backing layer 22 is a bioplastic film, which included 1-10 wt % alginate and 1-5 wt % carboxymethylcellulose crosslinked by 1-15% $CaCl_2$. Additives can be used in the backing layer to radiate or reflect heat, improve rehydration capacity, and improve texture into the bioplastic film. Examples of the additives in the backing layer 22 include, but are not limited to, kaolin clay, barium sulfate, calcium carbonate, zinc oxide, xanthan gum, or a combination thereof.

A bioglue was used to make the first adhesive layer 20. The bioglue included a solution of 1-5 wt % chitosan with 1-10 wt % glycerin (1:1.5 ratio).

The hydrogel used for the hydrogel layer 10 comprises polyacrylamide with an exemplary composition as follows (in wt % of overall hydrated gel): acrylamide, 10-14, water, 62-70, TEMED, 0.04, $CaCl_2$ or $CaCl_2$-6$H_2O$, 0-6, strontium chloride hexahydrate, 0-0.2, NaCl, 0-0.3, MBAA, 0.005-0.02, APS, 0.08-0.2, and $CaSO_4$½$H_2O$, 0.15-0.6.

The second adhesive 30 used is a medical grade silicone or acrylic-based pressure sensitive adhesive.

The samples were prepared as follows. First, the polyacrylamide hydrogel (PAM) was prepared using the method described above including preparation of two sols: Sol A and Sol B. Sol A and Sol B were mixed in a ratio of 4:1, and the resulting mixture was poured into a mold of desired shape. The top of the solution was pressed with a lightweight plate to allow the hydrogel to gelate overnight at room temperature. The hydrogel from the mold (i.e., the solid gel portion) was removed and then soaked in DI water for 10 minutes, then rinsed with DI water thoroughly to remove residual monomers.

The chitosan-containing "glue" was made by mixing of 5% chitosan and 7% glycerin in 1% acetic acid solution.

The alginate-containing film as the backing layer was prepared using a solution of 10% alginate and 3% carboxymethylcellulose, which was cross-linked with 10% $CaCl_2$ solution in a flat mold.

Layer-by-layer assembly of a material composite as the cooling pad: a thin layer of chitosan glue (i.e., the first adhesive layer) was applied onto the alginate-CMC film (i.e., the backing layer), and was left to solidify overnight in a closed chamber at room temperature. The resulting structure having the bioplastic film and the chitosan glue was applied to the PAM-based hydrogel layer and stored overnight in a closed chamber at room temperature.

The resulting material composite was cut into pieces having desired sizes and shapes. The second adhesive (layer 30) was applied to another surface of the hydrogel layer.

The second adhesive can be applied in different patterns, for example, with a full coverage, or in strips, or with perforated holes to enhance permeability. In some embodiments, the second adhesive layer or film can be pressed onto the hydrogel surface. In some embodiments, an adhesive film may be treated with oxyplasma or UV light plus benzophenone, and then bonded onto the hydrogel layer. In some embodiments, a liquid adhesive can be coated onto the hydrogel surface and then cured.

Figure 7:
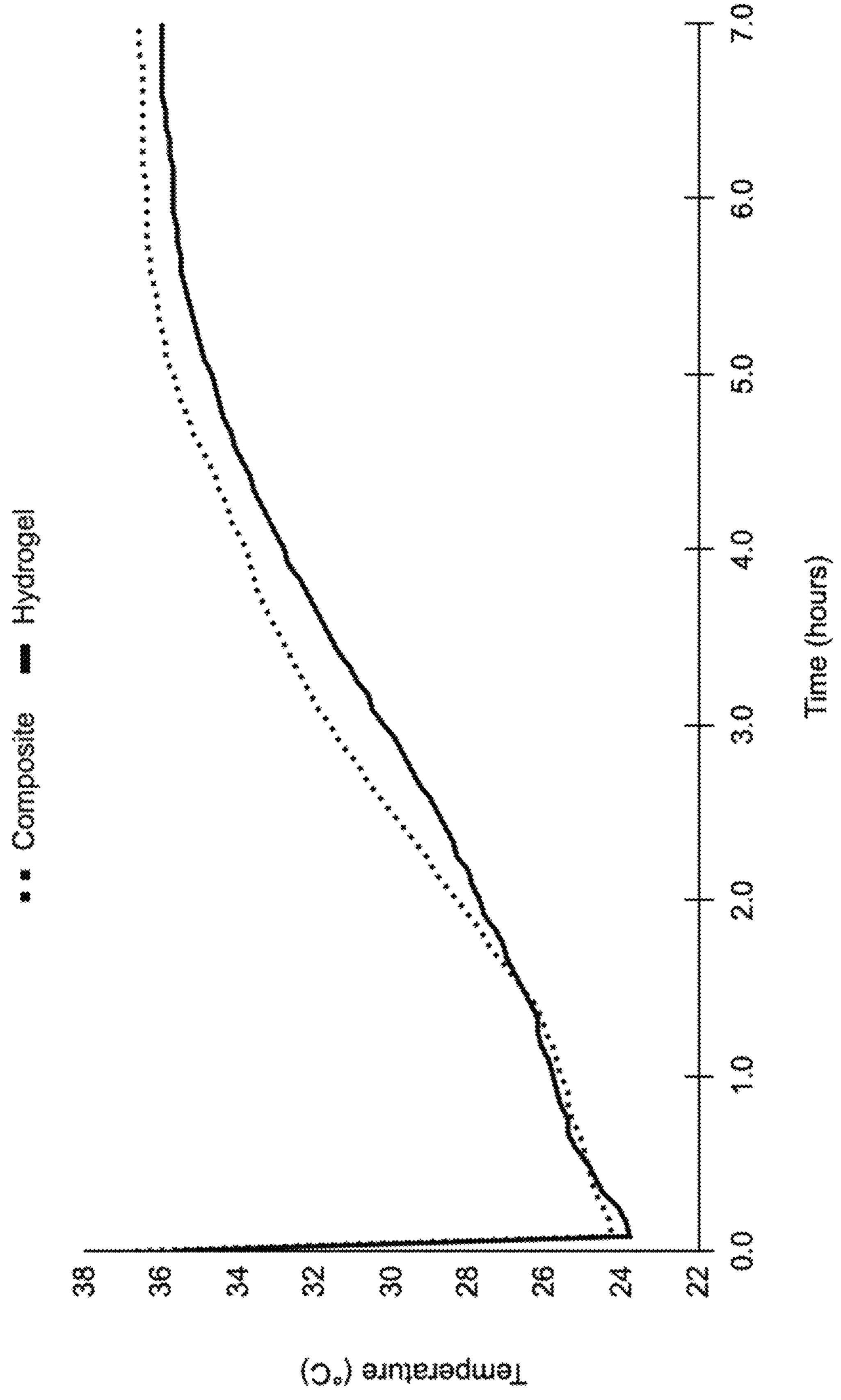
FIGS. 7-8 show in vitro experimental data and cooling effect of a hydrogel layer only and a cooling pad comprising the hydrogel and having a four-layer structure in accordance with some embodiments.
Figure 8:
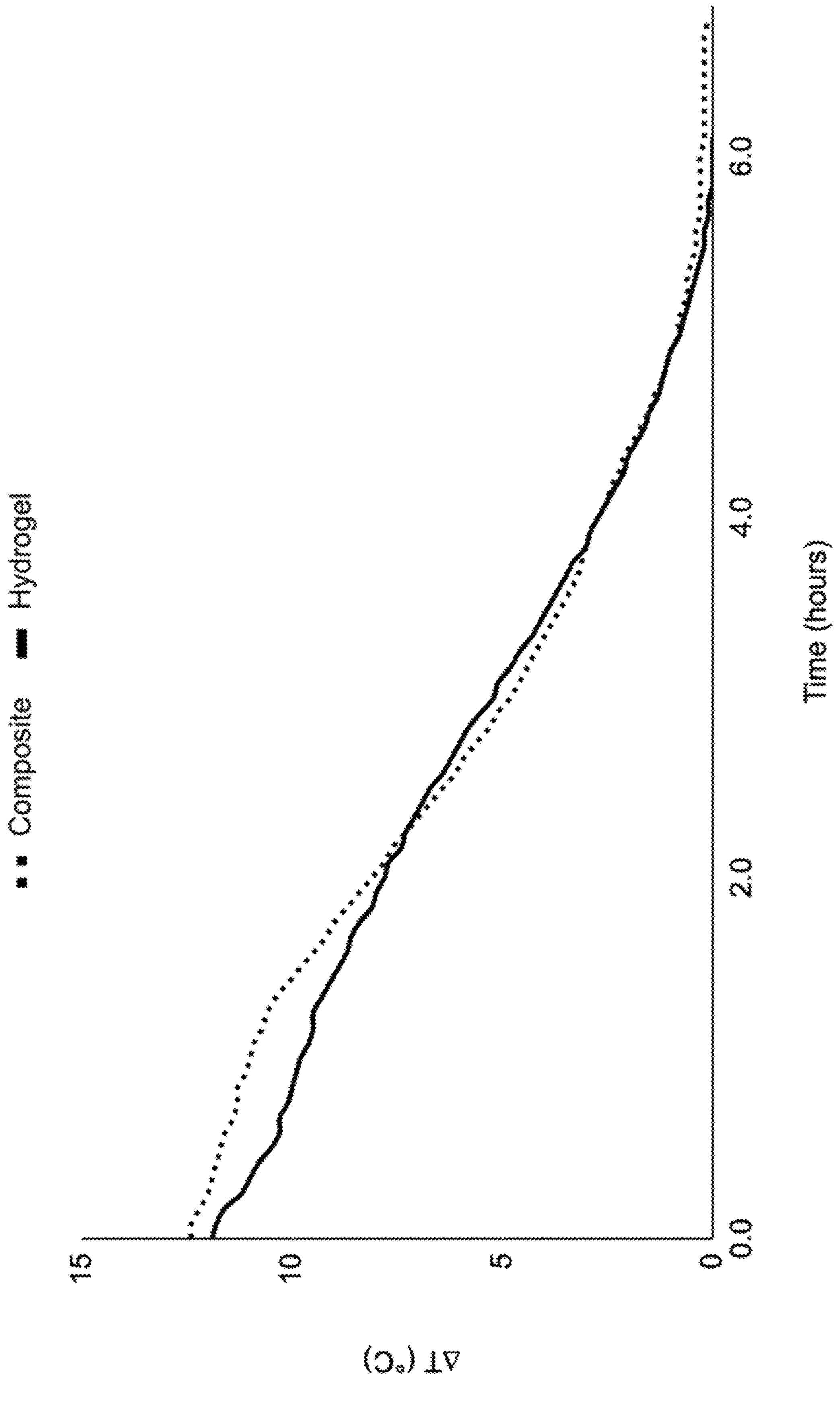

Referring to FIGS. 7-8, in vitro experimental data from an environmental chamber as a physiologic model show cooling effect of a hydrogel layer only and a cooling pad comprising the hydrogel and having a four-layer structure ("composite") in accordance with some embodiments. FIG. 7 shows the profiles of temperature versus time. FIG. 8 shows the temperature change versus time. The cooling effect can last as long as six hours before the temperature returns to the original temperature. The hydrogel of a single layer and the resulting cooling pad having the four-layer structure are similar to each other in overall cooling performance.

The cooling pad provided in the present disclosure can be used by a healthy human being such as an athlete, or a patient in need at home, remote or hospital setting. It can be also used for a patient during or after a surgery. For example, the cooling pad may be used for a patient during emergency situations where cooling is needed but ice and electricity-based cooling methods are not readily available. Such a cooling pad may be also used to reduce organ metabolism, for example, during cardiac surgery to reduce heart metabolism.

Although the subject matter has been described in terms of exemplary embodiments, it is not limited thereto. Rather, the appended claims should be construed broadly, to include other variants and embodiments, which may be made by those skilled in the art.

What is claimed is:

1. A cooling pad, comprising:

a hydrogel layer configured to provide cooling, the hydrogel layer comprising a solid gel portion and a liquid portion comprising water, wherein the liquid portion is embedded and distributed within the solid gel portion, and the solid gel portion comprises a base polymer as a first base ingredient for the hydrogel layer, moieties of a second base ingredient for the hydrogel layer, and an additive or filler;

a protective backing layer coated with a first adhesive layer disposed on a first side of the hydrogel layer, the first adhesive layer disposed between the hydrogel layer and the protective backing layer; and a second adhesive layer disposed on a second side of the hydrogel layer, the second side being opposite to the first side, wherein the protective backing layer is a bioplastic film comprising alginate and/or carboxymethylcellulose crosslinked by calcium chloride, and wherein the first adhesive layer is a bioglue comprising chitosan.

2. The cooling pad of claim 1, wherein the base polymer in the hydrogel layer is selected from the group consisting of polyacrylamide (PAM), poly(N-isopropylacrylamide) (PNIPAM), polyvinyl alcohol (PVA), oligo(ethylene glycol) methacrylate (OEGMA), 2-(2-methoxyethoxy) ethyl methacrylate (MEO2MA), Xylan, carboxymethylcellulose sodium, and any combination thereof.

3. The cooling pad of claim 1, wherein the second base ingredient for the hydrogel layer is selected from the group consisting of a bisacrylamide, calcium alginate, hyaluronic acid, 2-acrylamido-2-methylpropane sulfonic acid (AMPS), ethylene glycol-modified pillar[5]arene, and any combination thereof.

4. The cooling pad of claim 1, wherein the additive or filler is selected from the group consisting of $CaSO_4$, calcium chloride hexahydrate, LiCl, KCl, zinc oxide, carbon nanotube, $CaCl_2$, calcium chloride hydrate, LiBr, $MgCl_2$, silica microsphere, antimony-tin oxide nanoparticle, graphene oxide, tungsten bronze nanorods, and any combination thereof.

5. The cooling pad of claim 1, wherein the base polymer in the hydrogel layer is polyacrylamide (PAM), and the second base ingredient comprises a bisacrylamide as a crosslinker.

6. The cooling pad of claim 5, wherein the solid gel portion comprises 0.1%-25% of an antimicrobial agent, based on a total weight of the solid gel portion on a dry weight basis.

7. The cooling pad of claim 5, wherein the hydrogel layer has covalent crosslinks as a single type of crosslinking structure.

8. The cooling pad of claim 5, wherein the solid gel portion comprises 50%-80% of the moieties of the acrylamide, 0.1%-1% of the moieties of the bisacrylamide, 0.1%-20% of an absorbing agent, and 0.1%-25% of an antimicrobial agent, based on a total weight of the solid gel portion on a dry weight basis.

9. The cooling pad of claim 5, wherein the second base ingredient includes an alginate, the hydrogel layer has both covalent and ionic crosslinking structures.

10. The cooling pad of claim 1, wherein the additive or filler comprises a moisture absorbing agent selected from the group consisting of calcium sulfate, calcium chloride, potassium chloride, any hydrates thereof, and any combination thereof.

11. The cooling pad of claim 1, wherein the additive or filler comprises a stabilizing agent selected from strontium chloride hexahydrate, NaCl, and any combination thereof, and/or an antimicrobial agent selected from zinc oxide, titanium oxide, and any combination thereof.

12. The cooling pad of claim 1, wherein the hydrogel layer comprises at least 50% of a liquid portion based on a total weight of the hydrogel layer.

13. The cooling pad of claim 10, wherein the hydrogel layer comprises 80% to 86% of the liquid portion based on the total weight of the hydrogel layer.

14. The cooling pad of claim 1, wherein the protective backing layer is an alginate film.

15. The cooling pad of claim 1, wherein the second adhesive layer comprises an adhesive selected from the group consisting of a medical grade acrylic-based or silicone-based pressure sensitive adhesive, polyacrylic acid, thermoplastic hot melt adhesive, chitosan, polyallylamine, polyethylenimine, collagen, gelatin, and any combination thereof.

16. The cooling pad of claim 1, wherein the second adhesive layer comprises a silicone pressure sensitive adhesive.

17. A method of making the cooling pad of claim 1, comprising:

forming the hydrogel layer;

coating the first adhesive layer onto the protective backing layer;

applying the protective backing layer coated with the first adhesive layer onto the first side of the hydrogel layer; and coating the second adhesive layer on the second side of the hydrogel layer.

18. The method of claim 17, wherein forming the hydrogel layer comprises mixing at least two portions of sols, the at least two portions of sols comprise a first portion of sol comprising the first base ingredient, and a second portion of sol comprising the second base ingredient, each sol comprises water, and the first portion of sol comprises an acrylamide and the second portion of sol comprising a bisacrylamide.

19. A pack comprising an enclosure and the cooling pad of claim 1 enclosed therein.

20. The pack of claim 19, further comprising a release film disposed on the second adhesive layer.

* * * * *